(12) United States Patent    (10) Patent No.: US 7,813,811 B2
Wingeier et al.    (45) Date of Patent: Oct. 12, 2010

(54) REFILLABLE RESERVOIR LEAD SYSTEMS

(75) Inventors: Brett M. Wingeier, San Francisco, CA (US); Martha J. Morrell, Atherton, CA (US); C. Lance Boling, San Jose, CA (US)

(73) Assignee: NeuroPace, Inc., Mountain View, CA (US)

( * ) Notice: Subject to any disclaimer, the term of this patent is extended or adjusted under 35 U.S.C. 154(b) by 540 days.

(21) Appl. No.: 11/704,534

(22) Filed: Feb. 8, 2007

(65) Prior Publication Data

US 2008/0195160 A1    Aug. 14, 2008

(51) Int. Cl.
*A61N 1/00*    (2006.01)
(52) U.S. Cl. ..................................... 607/116
(58) Field of Classification Search ............ 607/43, 607/117, 3, 56, 137, 17, 116, 120, 127, 2; 604/500–503, 96.01, 103.01, 103.06, 21, 604/103.08, 890.1; 424/130.1, 464, 473, 424/447, 448, 449, 368, 423; 310/328; 600/301, 600/573; 606/41, 119, 120, 127
See application file for complete search history.

(56) References Cited

U.S. PATENT DOCUMENTS

| | | | |
|---|---|---|---|
| 3,310,051 A | | 3/1967 | Schulte |
| 3,640,269 A | * | 2/1972 | Delgado ..................... 600/573 |
| 4,506,680 A | | 3/1985 | Stokes |
| 5,092,332 A | | 3/1992 | Lee et al. |
| 5,217,028 A | | 6/1993 | Dutcher et al. |
| 5,255,693 A | | 10/1993 | Dutcher et al. |
| 5,265,608 A | | 11/1993 | Lee et al. |
| 5,496,360 A | * | 3/1996 | Hoffmann et al. ........... 607/120 |
| 5,713,847 A | | 2/1998 | Howard, III et al. |
| 5,755,758 A | | 5/1998 | Woloszko et al. |
| 5,834,051 A | | 11/1998 | Woloszko et al. |
| 5,836,935 A | | 11/1998 | Ashton et al. |
| 5,865,842 A | * | 2/1999 | Knuth et al. ................. 607/116 |
| 6,006,124 A | | 12/1999 | Fischell et al. |
| 6,032,482 A | | 3/2000 | Krauss |
| 6,038,482 A | | 3/2000 | Vachon |
| 6,068,853 A | * | 5/2000 | Giannos et al. ............. 424/449 |
| 6,073,048 A | * | 6/2000 | Kieval et al. .................. 607/17 |

(Continued)

OTHER PUBLICATIONS

Anonymous. (2006). "Ommaya Reservoir," located at <http://health.enotes.com/cancer-encyclopedia/ommaya-reservoir>, last visited on Sep. 18, 2006, six pages.

(Continued)

*Primary Examiner*—George Manuel
*Assistant Examiner*—Robert N Wieland

(57) ABSTRACT

Medical electrical lead systems and related methods are described. The medical electrical lead systems may be configured to be at least partially implanted in a body of a subject. Some variations of the medical electrical lead systems may comprise a lead body comprising a proximal end and a distal end and a lumen extending at least partially therebetween, at least one electrode in the proximity of the distal end of the lead body, and a reservoir in fluid communication with the lumen, where the reservoir is located at a position removed from the distal end of the lead body. Certain variations of the medical electrical lead systems may comprise a lead body comprising a proximal end and a distal end and first and second lumens extending at least partially therebetween, and at least one electrode in the proximity of the distal end of the lead body.

24 Claims, 21 Drawing Sheets

U.S. PATENT DOCUMENTS

| | | | |
|---|---|---|---|
| 6,148,231 | A | 11/2000 | Henley |
| 6,168,801 | B1 | 1/2001 | Heil, Jr. et al. |
| 6,219,577 | B1 | 4/2001 | Brown, III et al. |
| 6,227,203 | B1 | 5/2001 | Rise et al. |
| 6,304,787 | B1 | 10/2001 | Kuzma et al. |
| 6,330,471 | B1 | 12/2001 | Higo et al. |
| 6,385,491 | B1 | 5/2002 | Lindemands et al. |
| 6,497,699 | B1 | 12/2002 | Ludvig et al. |
| 6,567,705 | B1* | 5/2003 | Stokes et al. ............... 607/120 |
| 6,571,125 | B2 | 5/2003 | Thompson |
| 6,635,045 | B2 | 10/2003 | Keusch et al. |
| 6,678,553 | B2 | 1/2004 | Lerner et al. |
| 6,685,648 | B2* | 2/2004 | Flaherty et al. ............. 600/464 |
| 6,726,678 | B1* | 4/2004 | Nelson et al. ............ 604/891.1 |
| 6,748,653 | B2 | 6/2004 | Lindemands et al. |
| 6,931,286 | B2 | 8/2005 | Sigg et al. |
| 6,944,497 | B2 | 9/2005 | Stypulkowski |
| 7,010,356 | B2 | 3/2006 | Jog et al. |
| 7,044,942 | B2 | 5/2006 | Jolly et al. |
| 7,066,904 | B2* | 6/2006 | Rosenthal et al. ...... 604/103.08 |
| 7,200,432 | B2 | 4/2007 | Lerner et al. |
| 7,241,283 | B2 | 7/2007 | Putz |
| 7,337,011 | B2* | 2/2008 | Stokes et al. ............... 607/120 |
| 2003/0236496 | A1* | 12/2003 | Samson et al. ......... 604/103.02 |
| 2004/0127942 | A1* | 7/2004 | Yomtov et al. ................. 607/3 |
| 2004/0248326 | A1* | 12/2004 | Ziaie et al. ..................... 438/1 |
| 2005/0070985 | A1 | 3/2005 | Knapp et al. |
| 2005/0149157 | A1 | 7/2005 | Hunter et al. |
| 2005/0246003 | A1 | 11/2005 | Black et al. |
| 2005/0246004 | A1 | 11/2005 | Cameron et al. |
| 2005/0277912 | A1* | 12/2005 | John ....................... 604/890.1 |
| 2006/0058856 | A1 | 3/2006 | Morrell |
| 2006/0095105 | A1 | 5/2006 | Jog et al. |
| 2006/0129204 | A1 | 6/2006 | Pless et al. |
| 2006/0155343 | A1* | 7/2006 | Vilims ......................... 607/43 |
| 2006/0184143 | A1 | 8/2006 | Jolly et al. |
| 2007/0060815 | A1 | 3/2007 | Martin et al. |
| 2007/0088335 | A1 | 4/2007 | Jolly |
| 2007/0250136 | A1* | 10/2007 | Karunasiri et al. ............ 607/56 |
| 2008/0015540 | A1* | 1/2008 | Muni et al. ................. 604/500 |
| 2008/0033520 | A1* | 2/2008 | Jolly ......................... 607/137 |
| 2008/0097280 | A1 | 4/2008 | Martin et al. |

OTHER PUBLICATIONS

Cavuoto, J. (Jan. 2002). "Biomaterials Key Factor in Next-Generation Electrodes," *Neurotech Business Report* 2(1):3-5.

Christensen, J. et al. (Oct. 2001). "Plasma Concentration of Topiramate Correlates with Cerebrospinal Fluid Concentration," *Therapeutic Drug Monitoring* 23(5):529-535.

Craighead, H.G. (Nov. 24, 2000). "Nanoelectromechanical Systems," *Science* 290:1532-1535.

Doose, D.R. et al. (2002). "Topiramate: Chemistry, Biotransformation, and Pharmacokinetics," Chapter 78, in *Antiepileptic Drugs*, $5^{th}$ Edition, Levy, R.H. et al. eds., Lippincott Williams & Wilkins: Philadelphia, PA, pp. 727-734.

Ghosh, S. et al. (May 2000). "Electrochemical Characterization of Poly(3,4-ethylene dioxythiophene) Based Conducting Hydrogel Networks," *J. of the Electrochem. Soc.* 147(5):1872-1877.

Gilmore, K. et al. (1994). "Preparation of Hydrogel/Conducting Polymer Composites," *Polymer Gels and Networks* 2(2):135-143.

Martin, D.C. et al. "Bio-Electronic Implantable Device Coating Applications," in White Paper: Bioactive Conducting Polymer Coatings for Biomedical Devices, University of Michigan, four pages. (in internal database as of Aug. 30, 2006).

Olsen, R.W. (2002). "Phenobarbital and Other Barbiturates: Mechanisms of Action," Chapter 50, in *Antiepileptic Drugs*, $5^{th}$ Edition, Levy, R.H. et al. eds., Lippincott Williams & Wilkins: Philadelphia, PA, pp. 489-495.

Pitt, W.G. et al. (Nov. 2004). "Ultrasonic Drug Delivery—A General Review," *Expert Opinion on Drug Delivery* 1(1):37-56.

Rusakov, D.A. et al. (May 1, 1998). "Extrasynaptic Glutamate Diffusion in the Hippocampus: Ultrastructural Constraints, Uptake, and Receptor Activation," *The J. of Neurosci.* 18(9):3158-3170.

Non-Final Office Action mailed on Feb. 23, 2010, for U.S. Appl. No. 11/704,549, filed Feb. 8, 2007, fourteen pages.

\* cited by examiner

REFILLABLE RESERVOIR LEAD SYSTEMS

TECHNICAL FIELD

The methods and devices described herein relate generally to the field of medical electrical lead systems that may be at least partially implanted in a body of a subject. More specifically, the methods and devices described herein relate to medical electrical lead systems for treatment of neural tissue, such as brain tissue, where the medical electrical lead systems include at least one reservoir that may be used to release at least one bioactive agent into the neural tissue. The methods and devices described herein may have particular utility in the area of treatment of neurological disorders.

BACKGROUND

Neurological disorders are prevalent in the United States and around the rest of the world, with millions of people suffering from various types of neurological disorders of varying severity. A person who has a neurological disorder may be substantially debilitated, and may experience a significant decline in quality of life.

One example of a neurological disorder is epilepsy, which is characterized by the occurrence of seizures. Because epilepsy is characterized by seizures, its sufferers can be limited in the kinds of activities in which they may participate. For example, an epileptic may have limited or no ability to drive, work, or participate in recreational activities. Some epilepsy sufferers have serious seizures with such high frequency that they are effectively incapacitated. Additionally, in some cases, epilepsy is progressive, and can be associated with degenerative disorders and conditions. Over time, epileptic seizures may become more frequent and serious, and in particularly severe cases, may lead to the deterioration of other brain functions, as well as physical impairment.

Drug therapy and surgery are examples of current methods that may be used to treat epilepsy. Various antiepileptic drugs are available, and may be administered, for example, at the onset of pre-seizure symptoms or auras, to mitigate the effects of epilepsy. Surgical procedures include radical surgical resections, such as hemispherectomies, corticectomies, lobectomies and partial lobectomies, as well as less radical procedures, including lesionectomies, transections, and stereotactic ablation. An additional procedure that may be used to treat epilepsy is electrical stimulation, in which seizures may be treated and/or terminated by applying electrical stimulation to the brain. Typically, the detection and responsive treatment of seizures via electrical stimulation can include analysis of electroencephalogram (EEG) waveforms and electrocorticogram (ECoG) waveforms. An EEG waveform includes signals representing aggregate neuronal activity potentials detectable via electrodes applied to a patient's scalp, and/or signals obtained from deep in a patient's brain via depth electrodes and the like. An ECoG waveform includes signals obtained from internal electrodes near the cortex of the brain (generally on or under the dura mater), and/or brain signals from deeper structures.

Generally, it is preferable to detect and treat a seizure at or near its inception, or even before it has begun. The beginning of a seizure, or an onset, may be a clinical onset or an electrographic onset. A clinical onset represents the beginning of a seizure as manifested through observable clinical symptoms, such as involuntary muscle movements or neurophysiological effects such as lack of responsiveness. An electrographic onset, which typically occurs before a clinical onset and which may enable intervention before the patient suffers symptoms, refers to the beginning of detectable electrographic activity indicative of a seizure.

Epilepsy is only one example of a neurological disorder. Additional examples of neurological disorders include movement disorders (e.g., Parkinson's disease), psychiatric disorders, sleep disorders, and language disorders. As briefly discussed above, these and other neurological disorders can severely disrupt a person's quality of life. Thus, it would be preferable to provide a relatively simple method of treating neurological disorders, whether by a physician or by the person suffering from the neurological disorder. It also would be desirable to provide a relatively easy method of initiating treatment upon the onset of symptoms, and/or to provide a method that allows for continuous treatment at selected intervals over a period of time.

BRIEF SUMMARY

Described here are medical electrical lead systems for treatment of neurological disorders, as well as related methods. The medical electrical lead systems may be configured to be at least partially implanted in a body of a subject. For example, the medical electrical lead systems may be configured to be at least partially implanted into neural tissue, such as brain tissue. The lead systems may be used to release one or more bioactive agents, such as one or more therapeutic agents, into the body of the subject. These bioactive agents may be released in conjunction with the application of other treatment methods, such as electrostimulation, or may be released independently of any other treatment methods.

The lead systems generally comprise a lead body and at least one electrode. In some variations of the lead systems, the lead body may comprise a lumen that extends at least partially between the proximal and distal ends of the lead body, and the electrode may be in the proximity of the distal end of the lead body. Such variations of the lead systems may further comprise a reservoir in fluid communication with the lumen, where the reservoir is located at a position removed from the distal end of the lead body, and/or where the reservoir is configured to be disposed between a cranium of a subject and a scalp of the subject when the lead system is at least partially implanted in the body of the subject. Certain variations of the lead systems may comprise at least two lumens extending at least partially between the proximal and distal ends of the lead body, with the electrode being in the proximity of the distal end of the lead body.

As described above, the methods described herein may be used to treat one or more neurological disorders in a subject. Some variations of the methods may be used to treat epilepsy, and may comprise at least partially implanting a medical electrical lead system in a brain of a subject, and detecting epileptiform activity or an electrographic seizure in the brain of the subject. The lead system may comprise a lead body comprising a lumen that is in fluid communication with a refillable reservoir, and may be configured to deliver at least one bioactive agent to the brain upon detection of epileptiform activity or an electrographic seizure. Certain variations of the methods may include at least partially implanting a medical electrical lead system in a brain of a subject, the lead system comprising a lead body comprising a lumen and a reservoir that is in fluid communication with the lumen of the lead body, the reservoir containing at least one bioactive agent, where the lead system is configured to allow the bioactive agent to passively advance from the lumen of the lead body into a brain of a subject. When the bioactive agent passively advances through the lead system, the bioactive agent moves (e.g., flows) through the lead system without any external force being applied to it. In other words, while the bioactive agent may flow through one or more valves and/or membranes, the bioactive agent is not actively advanced through the lead system (e.g., using a pump). The use of passive advancement may be advantageous because it may allow for relatively simple bioactive agent delivery.

In some variations of the lead systems, the reservoir may be located in the proximity of the proximal end of the lead body and/or may be configured to be implanted in a skull of a subject. The reservoir may be integral with the lead body or may be attached to the lead body. The lead systems may include one reservoir or more than one reservoir, such as two or three reservoirs. Certain variations of the lead systems may include at least two reservoirs, with at least one of the reservoirs being located at a position distal of at least one of the other reservoirs. The lead system may include one or more reservoirs that are configured to be activated by a pump. In some variations, a reservoir may be in the form of a lumen of a lead body, or may be in the form of a protrusion extending from a lumen of a lead body. The reservoirs may be refillable. Certain variations of the reservoirs may be configured to be secured to a skull of a subject. In some variations, a reservoir and a lumen of a lead body may be separated by a valve, such as a valve that is configured to open when the valve is exposed to a magnet. In such variations, the valve itself may also comprise a magnet. A lumen may or may not extend along the entire length of a lead body.

The lead systems may be configured to deliver at least one bioactive agent to a body of a subject. The bioactive agent may be allowed to passively advance from a reservoir through a lumen of a lead body. For example, the lead systems may be configured to release at least one bioactive agent by at least one of diffusion, elution, or effusion. In certain variations, the lead systems may be configured to allow the bioactive agent to passively advance from a lumen of a lead body into the brain of a subject at or near a predetermined rate or at predetermined intervals. For example, the lead systems may include one or more valves that allow the bioactive agent to passively advance through the lead systems at selected intervals.

The bioactive agent may comprise at least one antiepileptic drug, such as acetazolamide, carbamazepine, clonazepam, clorazepate, benzodiazepine derivatives (e.g., diazepam), divalproex, ethosuximide, ethotoin, felbamate, fosphenytoin, gabapentin, lamotrigine, levetiracetam, mephobarbital, methsuximide, oxcarbazepine, phenacemide, phenobarbital, phenytoin, pregabalin, primidone, thiopental, tiagabine, topiramate, trimethadione, valproate, zonisamide, tetrodotoxin, allopregnanolone, ganaxolone, or a combination thereof. The bioactive agent may comprise a benzodiazapene or a barbiturate. In some variations, the bioactive agent may be adapted to facilitate neurostimulation, and/or to facilitate the recording of one or more signals from a brain of a subject.

Certain variations of the lead systems may comprise at least one conductor disposed within the lead body. The conductor may be wound or coiled around a lumen of the lead body. The lead body may comprise at least one polymer. In some variations, the lead body may comprise silicone. In certain variations, the distal end of the lead body may be formed of at least one permeable material, and/or the proximal end of the lead body may be formed of at least one substantially impermeable material. In some variations, the electrode may be permeable. In certain variations, the lead system may be configured to be connected to an implantable medical device. The reservoir may be secured to the implantable medical device. Alternatively or additionally, the reservoir may be secured to tissue. The reservoir may be configured to be at least partially implanted (e.g., fully implanted) in a body of a subject.

The lead systems may be, for example, cortical strip leads, such as cortical strip leads having a distal end comprising a permeable portion (e.g., comprising permeable silicone) and a substantially impermeable portion (e.g., comprising substantially impermeable silicone). The permeable portion may be configured to contact brain tissue when positioned within a brain of a subject, and/or the substantially impermeable portion may be configured to contact the dura mater when positioned within a brain of a subject.

The method may comprise applying neurostimulation to a region of the brain and/or recording signals from a region of the brain. In certain variations, the method may comprise refilling the refillable reservoir with the bioactive agent. The refillable reservoir may be refilled, for example, by injecting the refillable reservoir with the bioactive agent. In some variations in which the reservoir comprises a protrusion, the method may comprise applying pressure to the protrusion to result in advancement of the bioactive agent from the lumen of the lead body into the brain. In certain variations, the method may further comprise electrostatically drawing the bioactive agent out of the reservoir.

The subject may have any of a number of neurological disorders, such as epilepsy, movement disorders (e.g., Parkinson's disease, dystonia, or tremors such as essential tremor), psychiatric disorders (e.g., bipolar disorder or depression, such as major depression disorder), sleep disorders, language disorders, Tourette's syndrome, etc. Other conditions may also be treated using the lead systems and methods described herein, including, for example, migraine headaches and/or chronic pain.

BRIEF DESCRIPTION

DETAILED DESCRIPTION

Described here are devices and related methods for treating neurological disorders with one or more bioactive agents. The devices generally are medical electrical lead systems including lead bodies having at least one lumen and a reservoir that is in fluid communication with the lumen. The lead systems may be used to deliver one or more bioactive agents to a target site, such as neural tissue (e.g., brain tissue). The reservoirs may store the bioactive agent or agents, and/or may be refillable. The reservoirs may allow the lead systems to provide a continuous supply of bioactive agent to a target site, and/or to provide bioactive agent to a target site as needed, according to a schedule, and/or at predetermined intervals. The lead systems may be connected to one or more implantable medical devices, such as electrostimulation devices or recording devices, which allow the lead systems to provide one or more other treatments, in addition to the bioactive agent treatment.

Figure 1:
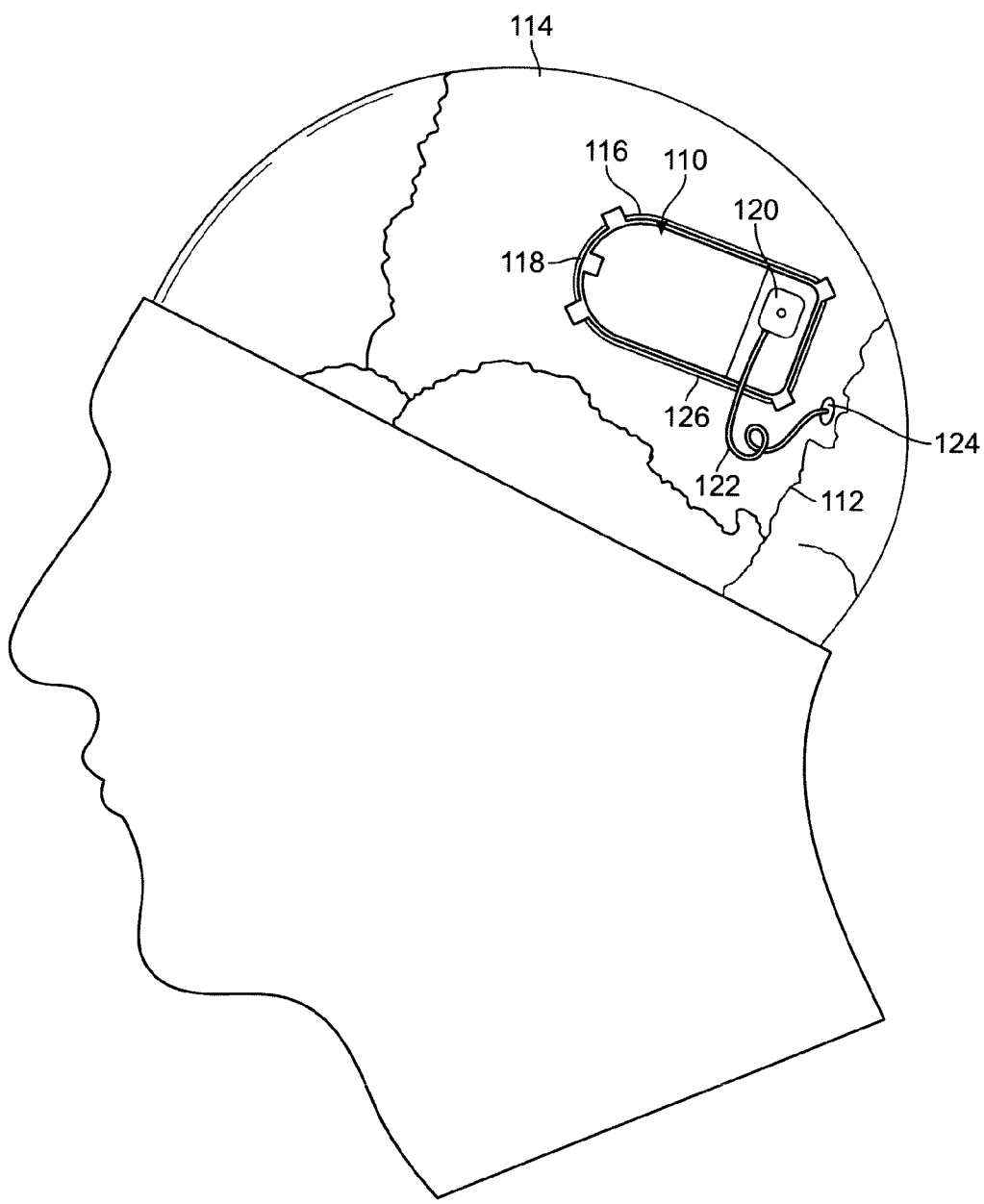
FIG. 1 is an illustration of a cranium of a subject, showing an implantable neurostimulation device as implanted, and a medical electrical lead system connected to the implantable neurostimulation device and extending to the brain of the subject.

Turning now to the figures, FIG. 1 shows an implantable medical device (110), such as an electrostimulation device, affixed to a cranium (114) of a subject by way of a ferrule (116). Ferrule (116) is a structural member that is adapted to fit into a cranial opening, attach to the cranium, and retain device (110). One example of a method that may be used to implant device (110) and affix it to cranium (114) includes performing a craniotomy in the parietal bone (not shown) anterior to the lamboid suture (112) to define an opening (118) slightly larger than device (110), inserting ferrule (116) into opening (118), and affixing ferrule (116) to cranium (114). After ferrule (116) has been affixed to cranium (114), device (110) is inserted into, and affixed to, the ferrule. The presence of ferrule (116) may, for example, help to ensure that device (110) is tightly and securely implanted.

As shown in FIG. 1, device (110) includes an outer housing (126), and a lead connector (120) configured to receive one or more electrical lead systems. Housing (126) may provide protection to the components of device (110), and may be formed of, for example, one or more metals, such as titanium. Additionally, housing (126) may enclose a battery and any electronic circuitry that may be required or desired to provide device (110) with its functionality. In some variations, a telemetry coil may be located in the interior of device (110), or may be provided outside of housing (126) and integrated with lead connector (120), to facilitate communication between device (110) and external devices.

Figure 2:
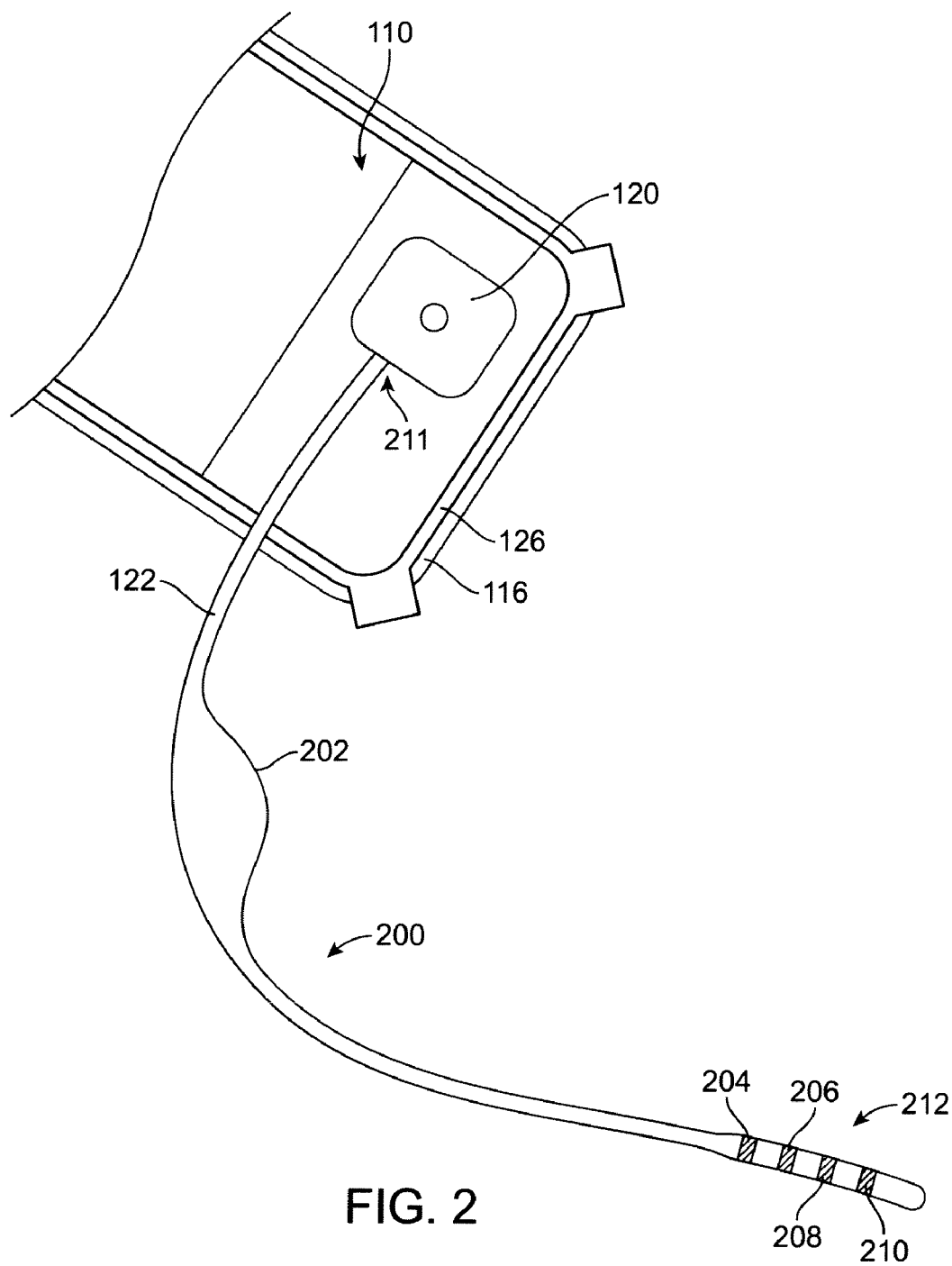
FIG. 2 is a partial top view of the device and lead system of FIG. 1.

In FIG. 1, lead connector (120) is connected to a lead body (122) of a medical electrical lead system (200) (shown in FIG. 2). Lead body (122) extends through a burr hole (124) or other opening in cranium (114). Though not shown, in FIG. 2, the portion of lead body (122) that extends past burr hole (124) is coupled to four electrodes that are implanted into a desired location in the subject's brain. If the length of lead body (122) is substantially greater than the distance between device (110) and burr hole (124), then any excess may be urged into a configuration, such as an uncoiled configuration, that consolidates the excess lead body (e.g., under the scalp). In some variations, burr hole (124) may be sealed after implantation to limit or prevent further movement by lead system (200). This sealing may be provided, for example, by affixing a burr hole cover apparatus to cranium (114) at least partially within burr hole (124). Burr hole sealing is described, for example, in U.S. Pat. No. 6,006,124, which is hereby incorporated by reference in its entirety.

Lead connector (120) helps to secure lead body (122) to device (110). Lead connector (120) also facilitates electrical connection between circuitry within device (110) and one or more conductors in lead body (122). The conductors, in turn, are coupled to one or more electrodes. Lead connector (120) may accomplish the above-described functions in a substantially fluid-tight environment and in a biocompatible manner.

In general, device (110) may be used to treat one or more neurological disorders. For example, device (110) may treat epilepsy by detecting epileptiform activity or an electrographic seizure from the brain, and applying neurostimulation to the brain. A device such as device (110) may be able to both sense epileptiform activity, and provide electrical stimulation to the brain in response. However, in some variations, separate devices may be used for monitoring brain activity and applying electrical stimulation or neurostimulation. Brain activity may be detected, for example, by comparing ongoing activity to typical epileptiform activity, including identifying characteristics of epileptiform activity or an electrographic seizure from ongoing brain activity. Once activity is detected, stimulation may be applied to the affected region. Additional stimulation to secondary brain regions may also be applied.

As described above, device (110) may be an electrostimulation device or neurostimulation device. Neurostimulation devices are described, for example, in U.S. Patent Application Publication No. US 2006/0058856 and U.S. patent application Ser. No. 11/525,586, both of which are hereby incorporated by reference in their entirety. Other examples of implantable medical devices include recording devices. Moreover, in some variations, an implantable medical device may be configured to detect and/or respond to neurological activity other than epileptiform activity, such as activity associated with movement disorders, psychiatric disorders, sleep disorders, language disorders, migraine headaches, and chronic pain. These are intended only to be illustrative examples, and are not intended to be limiting. Furthermore, some or all of the actions performed by a device may not be therapeutic. For example, the actions may involve data recording or transmission, providing warnings to the subject, or any of a number of alternative actions. In some variations, a neurostimulation device may not be a single device, but may be a system of component devices. Thus, a neurostimulation device may also function as a diagnostic device, and may be interfaced with external equipment.

While device (110) is shown as being affixed to cranium (114), devices may be positioned in any of a number of different places either within or outside of a body of a subject. For example, in some variations, a device may be implanted under a subject's scalp, but external to the subject's cranium. In certain variations (e.g., when it is not possible to implant a device intracranially), a device may be implanted pectorally, with leads extending through the subject's neck and between the subject's cranium and scalp, as necessary. Any other suitable positions for a device may also be used.

FIG. 2 shows an enlarged view of a portion of device (110), as well as lead system (200) including the lead body (122) shown in FIG. 1. As shown in FIG. 2, in addition to including lead body (122), which has a proximal end (211) and a distal end (212), lead system (200) also includes a reservoir (202) and multiple cylindrical electrodes (204), (206), (208), and (210) connected to the lead body at its distal end (212). Reservoir (202) is in the form of a protrusion on lead body (122), and is integral with lead body (122), such that the reservoir and the lead body form one unit. The integral reservoir and lead body may be formed, for example, by molding the lead body together with the reservoir, as one piece. In certain variations, an integral reservoir and lead body may be formed using an extrusion process. The wall thickness in the area of the lead body that is to serve as the reservoir can be extruded thinner than in other areas, then compressed air may be introduced into the lead body used to expand the thinned wall section so that it will retain its expandable shape. In other variations, transfer molding is used to form an integral reservoir and lead body. Transfer molding involves a hydraulic or pneumatic press having a lower platen and an upper platen. Uncured silicon rubber is placed into a reservoir within the lower platen. The mold, such as a book-mold, is placed on top of the lower platen. The mold has an opening in its underside to receive the material from which the reservoir and lead body will be formed, located so that the opening in the mold will match the opening of the reservoir in the lower platen when the mold is on top of the lower platen. When the press is actuated, the upper platen engages the topside of the mold and applies pressure to the mold. A piston contained within the reservoir is actuated and transfers the material from the reservoir into a cavity within the mold. The upper and lower platens are heated and the rubber cures. When the cure process is complete, the press is disengaged and the mold is removed from the press to recover the finished component. In still other variations, compression molding can be used wherein the material from which the integral lead body and reservoir is to be formed is positioned between two plates and compressed between two halves of a mold and subsequently thermally cured to form the component.

Electrodes (204), (206), (208), and (210) are connected to conductors in the lead body, and may, for example, transmit electrical stimulation from device (110) to the brain of the subject. The electrodes of lead system (200) may be configured, for example, to sense brain activity, to apply neurostimulation, and/or to record brain signals. Electrodes may be formed of, for example, titanium, platinum, platinum alloyed with iridium, titanium nitride, iridium oxide, no nickel stainless steels, conductive organic materials (e.g., solid carbon), silicon, and/or any other materials and combinations of materials that are known to be suitable for use in electrodes. For example, an electrode may be formed of one material that is coated with another material. In certain variations, an electrode may be a semiconductor electrode. In some variations, one or more electrodes of a lead system may be formed of one or more permeable materials, such as permeable polymers. Specific examples of permeable materials that may be used in one or more of the electrodes include permeable silicone, silicone hydrogels, porous ceramics, permeable polyurethane, permeable polyethylene, and nanotubes. Any other appropriate permeable materials and combinations of materials may also be used. In certain variations, one or more electrodes of a lead system may be formed of one or more metallic electrode materials that have been sintered, such that the electrodes have at least one permeable or semi-permeable region. For example, the metallic electrode materials may be sintered to form a permeable or semi-permeable disc or plug. Furthermore, in some variations, a lead system may include one or more optical electrodes, or optodes, that are configured to optically measure signals. In such variations, the optodes may also be used to monitor bioactive agent levels. This monitoring of bioactive agent levels may be used, in turn, to control a pump or a valve in a lead system (both of which are further described below) using a feedback mechanism.

Reservoir (202) may contain one or more bioactive agents. During use of device (110), these agents may be delivered through lead body (122) and into a target site in the brain of the subject. As an example, if device (110) senses epileptic activity, then device (110) may initiate the delivery of an antiepileptic agent into the brain via lead system (200). For example, device (110) may provide a signal notifying the subject or the subject's physician that an antiepileptic agent should be administered. Alternatively or additionally, device (110) may initiate delivery of a stored antiepileptic agent from reservoir (202), through lead body (122), and into the brain. Device (110) may accomplish this in any of a number of different ways. As an example, in some variations, lead system (200) may include an electromechanical valve that is positioned to release bioactive agent from reservoir (202) into lead body (122), and that can be activated by device (110). As another example, in certain variations, reservoir (202) may be positioned near device (110), and/or between device (110) and the scalp of the subject in whom device (110) is implanted. Lead system (200) may include a ferromagnetic valve, and device (110) may include an electromagnet that is configured to pull the ferromagnetic valve open, thereby allowing bioactive agent to flow from reservoir (202) into lead body (122). As an additional example, in some variations, device (110) may be configured to withdraw bioactive agent from reservoir (202) using iontophoresis, using a repulsive electromotive force, or otherwise electrostatically by using a polarity difference or changing polarity to expel the agent from the reservoir. For example, a charged bioactive agent could be used, such as one containing the negatively charged valproate ion. An electrode may be located in or very near the reservoir and supplied with a negative charge, which will cause the agent to move away from the electrode. Alternatively, a positively charged electrode may be placed outside the reservoir that would attract the negatively charged bioactive agent and thus draw the bioactive agent out of the reservoir. In another variation, multiple electrodes may be provided and supplied with alternating positive and negative charges to meter the bioactive agent out of the reservoir and into the surrounding tissue at a predictable rate and in a predictable amount.

As shown, lead system (200) is configured to allow bioactive agents to passively advance from reservoir (202) through lead body (122), and into a target site in a body of a subject. The bioactive agents may exit the lead body through, for example, one or more apertures at its distal end. The bioactive agents may passively advance from the reservoir and through the lead body as a result of a bioactive agent gradient between the reservoir and the tissue of the subject. In other words, the tissue typically has a relatively low (or zero) concentration of bioactive agent, while the reservoir contains a relatively high amount of bioactive agent. Because of this gradient, the bioactive agent will advance from the area of high concentration (i.e., the reservoir) to the area of low concentration (i.e., the tissue). In some cases (e.g., in deep-brain applications), lead system (200) may be positioned so that reservoir (202) is higher than lead body (122). This height differential may enhance the advancement of bioactive agent from the reservoir into the lead body.

Lead systems may be configured to allow for the above-described passive advancement of bioactive agents (e.g., via diffusion, elution, and/or effusion), and/or may be configured to provide active advancement of bioactive agents from their reservoirs. For example, in some variations, a reservoir of a lead system may be configured to be activated by a pump, such that the pump can cause bioactive agents to flow out of the reservoir and into the lead body. As an example, a lead system may include an elastic reservoir and a pump that is in the form of a piezoelectric element positioned against the elastic reservoir and/or built into a wall of the reservoir. The reservoir, in turn, may include one or more check valves that control the direction of bioactive agent flow through the lead system. As the piezoelectric element oscillates, liquid can be drawn from a relatively large reservoir that also is part of the lead system, and that acts as a hydraulic reciprocating mechanism. As another example, a lead system including a reservoir may be positioned near an implantable device including a pump, such as an electromechanical diaphragm. The electromechanical diaphragm can exert pressure on the lead body and/or reservoir, which can cause bioactive agent within the lead body or reservoir to flow. As an additional example, some variations of lead systems may include a lead body and a reservoir that is integral with the lead body. The lead body may be connected to an implantable device, and the entire reservoir may be inserted into a pumping chamber that is part of the implantable device. The pumping chamber can be used to pump bioactive agent through the lead system (e.g., from the reservoir into the lead body). In such variations of lead systems, the implantable device may never come into contact with the bioactive agent, or may come into very limited contact with the bioactive agent.

Reservoir (202) may be used to store the bioactive agents and/or to release the bioactive agents over a selected period of time, and may also be refillable. In certain variations, such as when reservoir (202) contains tetrodotoxin as a bioactive agent, reservoir (202) may be configured to hold a relatively small volume of bioactive agent (e.g., on the order of 0.05 milliliter), while in other variations, reservoir (202) may be configured to hold a relatively large volume of bioactive agent (e.g., on the order of 25 milliliters). In some variations, reservoir (202) may be configured to hold a range of volumes of one or more bioactive agents, such as from about 0.05 milliliter to about 25 milliliters of bioactive agent. In one variation, the range of volumes the reservoir is capable of holding is from about 0.05 to 25 milliliters.

The bioactive agents that are delivered to a target site through a lead system may be any of a number of different types of bioactive agents, depending on the disorder or disorders which are desired to be treated.

As an example, in treatment of epilepsy, one or more of the bioactive agents typically would include an antiepileptic drug. Examples of antiepileptic drugs include acetazolamide, carbamazepine, clonazepam, clorazepate, benzodiazepine derivatives (e.g., diazepam), divalproex, ethosuximide, ethotoin, felbamate, fosphenytoin, gabapentin, lamotrigine, levetiracetam, mephobarbital, methsuximide, oxcarbazepine, phenacemide, phenobarbital, phenytoin, pregabalin, primidone, thiopental, tiagabine, topiramate, trimethadione, valproate, vigabatrin, zonisamide, tetrodotoxin, allopregnanolone, and ganaxolone.

Additional examples of bioactive agents include benzodiazapene and barbiturates. Furthermore, while certain bioactive agents described herein have been described as treating certain disorders, the bioactive agents described herein may be able to treat more than one type of disorder or condition. As an example, tetrodotoxin may be used to treat disorders other than epilepsy. Generally, the bioactive agents described herein may be employed when they can provide any function that is desirable and/or useful.

Still further examples of bioactive agents that may be used include bioactive agents that treat motor disorders (e.g., Parkinson's disease, dystonia, or tremors such as essential tremor), psychiatric disorders (e.g., bipolar disorder or depression, such as major depression disorder), language disorders, sleep disorders, and Tourette's syndrome. These are merely examples of different types of bioactive agents. Any other bioactive agents suitable for treating neurological disorders or other disorders of the body, or for providing other benefits, such as preventive care, may be used with the lead systems described herein as appropriate. For example, in some variations, bioactive agents having anti-inflammatory or antibiotic properties may be used. In certain variations, bioactive agents that may typically exhibit central nervous system (CNS) or systemic side effects, difficult deliverability, and/or unfavorable pharmacokinetics may be used with the lead systems described herein (e.g., because the lead systems can deliver the bioactive agents directly to a target location relatively efficiently).

Some bioactive agents may be used to facilitate neurostimulation. The bioactive agents may be delivered to neural tissue in conjunction with, prior to, and/or after, neurostimulation of the neural tissue. Examples of bioactive agents that may be used to facilitate neurostimulation include carbamazepine, oxcarbazepine, and phenytoin, which can inhibit rapid firing, and which may preferentially encourage a depolarization-block response to high-frequency neurostimulation (rather than a neural-firing response). Additional examples of bioactive agents that may be used to facilitate neurostimulation include glutamate-blocking agents such as lamotrigine and topiramate. These glutamate-blocking agents may diminish excitatory effects of neurostimulation. Further examples of bioactive agents that may be used to facilitate neurostimulation include GABAergic agents, such as topiramate, allopregnanolone, ganaxolone, benzodiazepines, barbiturates, tiagabine, or other agents which potentiate inhibition and which may be expected to potentiate inhibitory effects of neurostimulation.

Certain bioactive agents may be adapted to facilitate the recording of one or more signals from a brain of a subject, and thus may be used to enhance a recording procedure. These bioactive agents may also be delivered to neural tissue in conjunction with, prior to, and/or after, recording. Examples of bioactive agents that may facilitate recording (and that may also facilitate neurostimulation) include agents that limit or prevent an inflammatory response, and thereby also limit or prevent undesirable physical changes to the electrode-tissue interface. Examples of such bioactive agents include anti-inflammatory agents, antiproliferative agents (e.g., bone morphogenic proteins, ciliary neurotrophic factor, ribavarin, sirolimus, mycophenolate, mofetil, azathioprine, paclitaxel, and cyclophosphamide), and anti-gliotic agents. In some variations, one or more bioactive agents that facilitate brain signal recording may be delivered to neural tissue over a relatively long period of time, and may have a cumulative effect on the neural tissue.

Figure 25:
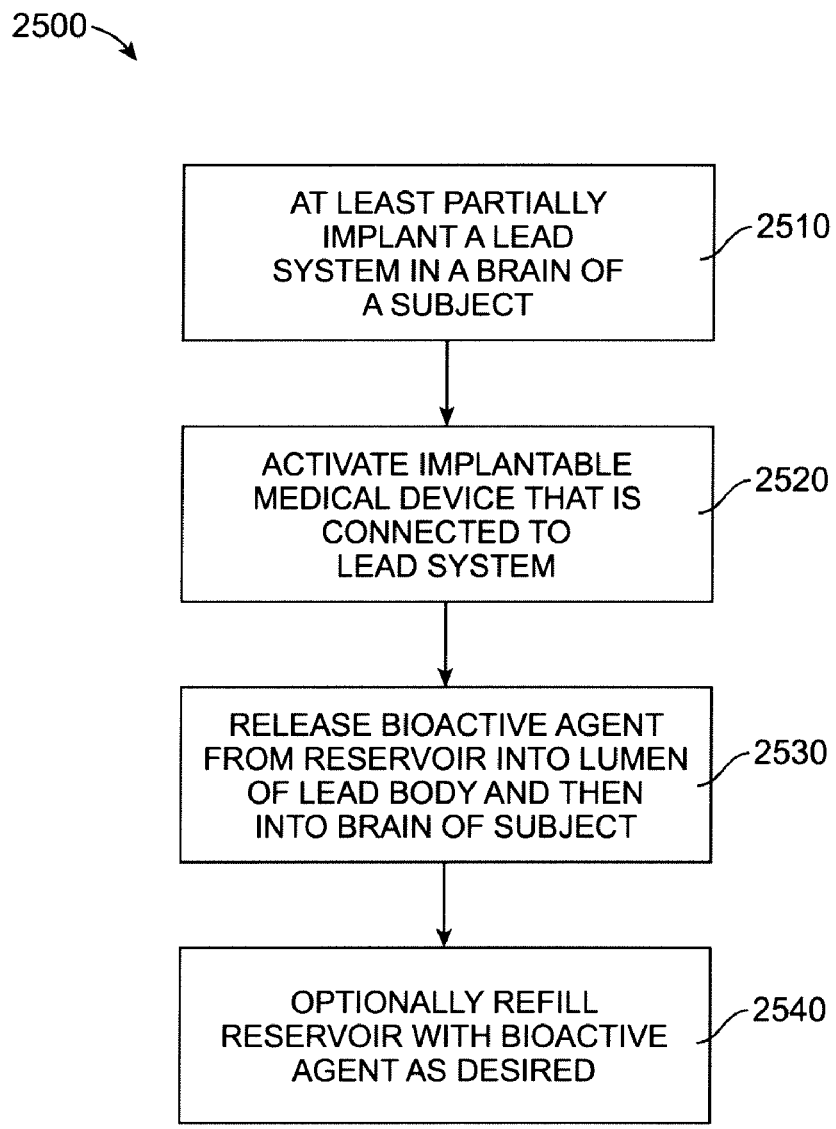
FIG. 25 is a flowchart representation of a method of using a lead system in a body of a subject.

Various methods may be employed to deliver one or more bioactive agents to a target site within a body of a subject, using one of the lead systems described herein. FIG. 25 provides a flowchart representation of one variation of such a method (2500). As shown there, method (2500) includes at least partially implanting a lead system in a brain of a subject (2510). The lead system includes a lead body and at least one reservoir, and is connected to an implantable medical device. The lead system may be entirely implanted in the brain of the subject, or at least one of its components may be located outside of the brain of the subject. For example, the reservoir of the lead system may be affixed to an exterior surface of the head of the subject. The implantable medical device may be partially or entirely implanted into the head of the subject, such as intracranially in the subject's parietal bone, in a location anterior to the lambdoid suture (as described, for example, with reference to FIG. 1 above).

After the lead system has been at least partially implanted in the brain of the subject, the medical device is activated (2520). The medical device may be configured, for example, to sense brain activity, such as epileptic activity. Method (2500) further includes releasing a bioactive agent from the reservoir of the lead system into a lumen of the lead body, and out into the brain of the subject (2530). The reservoir may be preloaded with the bioactive agent, and/or the method may include adding bioactive agent to the reservoir. For example, the medical device may provide an indication of epileptiform activity, and the method may include injecting one or more antiepileptic agents into the reservoir in response to the indication from the medical device. In some variations, the medical device may be configured to initiate release of bioactive agent from the reservoir, which may be preloaded with the bioactive agent, upon sensing certain brain activity. Method (2500) may further include refilling the reservoir as desired (2540), such as when the reservoir is empty, or at certain specific intervals according to a treatment protocol.

Referring back to FIG. 2, reservoir (202) is located at a position removed from distal end (212) of lead body (122). However, some variations of lead systems may include a lead body and a reservoir that is located at the distal end of the lead body, either in addition to or as an alternative to a reservoir that is located at a position removed from the distal end of the lead body. Furthermore, some lead systems may include a lead body and one or more electrodes that are located at a position removed from the distal end of the lead body.

Reservoirs and lead bodies may be formed of the same materials or different materials. In certain variations, a reservoir and/or lead body may be substantially formed of one or more insulating materials. In some variations, a reservoir and/or lead body of a lead system may be formed of one or more polymers, such as PTFE or ePTFE. In certain variations, a reservoir and/or a lead body may be formed of silicone. In some variations, a proximal end of a lead body may be formed of at least one substantially impermeable material (e.g., impermeable silicone or impermeable polyurethane), and/or a distal end of the lead body may be formed of at least one permeable material (e.g., permeable silicone or permeable polyurethane). Additional examples of substantially impermeable materials include Parylene polymer (from Para Tech Coating, Inc., Aliso Viejo, Calif.), engineered copolymers (e.g., polycarbonate urethane, polyetherurethane, silicone polycarbonate urethane, silicone polyether urethane), and various fluorocarbons. Additional examples of permeable materials that may be employed include permeable polytetrafluoroethylene and polytetrafluoroethylene variations, as well as sintered plastics, polyesters, nylons, etc. A lead body having an impermeable proximal end and a permeable distal end may, for example, allow one or more bioactive agents to be released only from its distal end. Other variations of lead bodies, however, may include at least one section that is proximal to their distal ends, and that is formed of at least one permeable material. Furthermore, while a lead body with apertures at its distal end has been described above, lead bodies may include one or more apertures at other locations, such as the proximal ends of the lead bodies.

Figure 3A:
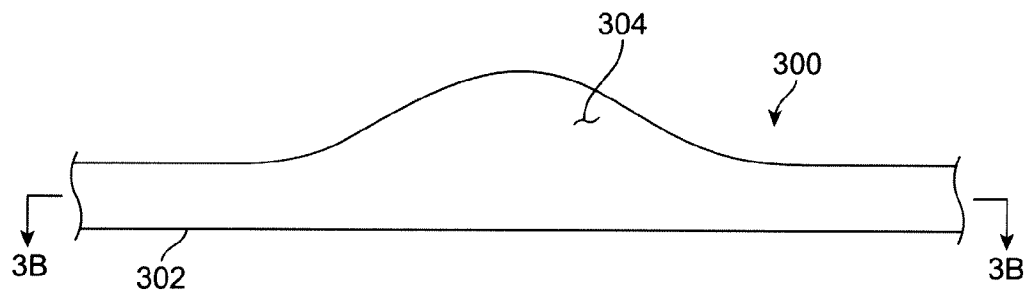
FIG. 3A is a side view of a portion of a medical electrical lead system.
Figure 3B:
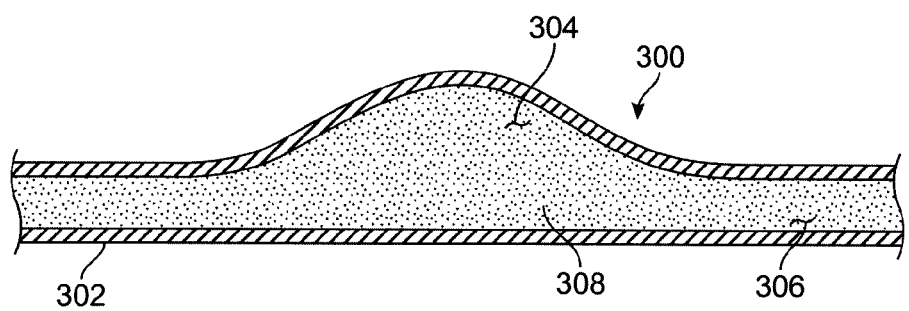
FIG. 3B is a cross-sectional view of the portion of the lead system of FIG. 3A, taken along line 3B-3B.

Different configurations, sizes, and shapes of reservoirs may be used in a lead system. For example, FIGS. 3A and 3B show a portion of a lead system (300) including a lead body (302) and a reservoir (304) that is integral with the lead body, such that the reservoir and the lead body together form one unit. Lead body (302) includes a lumen (306) that is in fluid communication with reservoir (304), thereby allowing reservoir (304) to provide lumen (306) with bioactive agent. As shown in FIG. 3B, a bioactive agent (308) is contained within both reservoir (304) and lumen (306).

Figure 4:
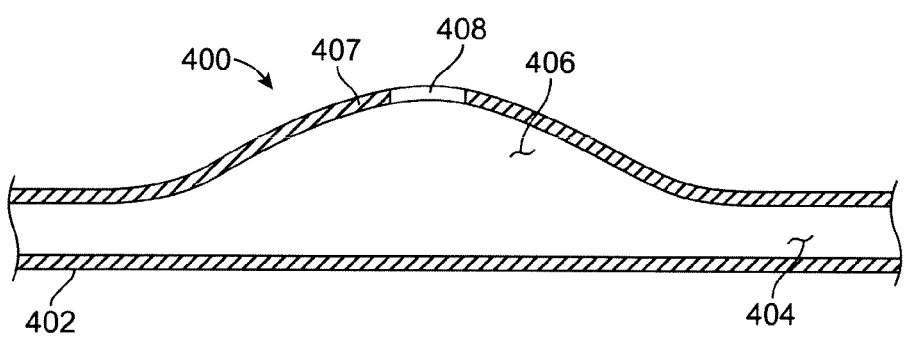
FIGS. 4-8 are cross-sectional views of portions of medical electrical lead systems.

As described above, some reservoirs may be refillable. For example, FIG. 4 shows a portion of a lead system (400) including a lead body (402) having a lumen (404), and a reservoir (406) that is integral with the lead body and in fluid communication with lumen (404). Reservoir (406) includes a sidewall (407) having a portion (408) that is configured for passage of a syringe needle therethrough. Portion (408) may be formed of, for example, a material that allows for relatively easy insertion of a syringe needle, such as silicone. The syringe may contain one or more bioactive agents, which may be injected into the reservoir through portion (408). Because reservoir (406) is in fluid communication with lumen (404), the bioactive agent can advance from reservoir (406) into lumen (404). Thus, a refillable reservoir may advantageously allow a physician to provide a relatively large amount of bioactive agent to a patient, without requiring a relatively large reservoir to do so. Furthermore, a refillable reservoir may allow additional bioactive agent to be provided to a patient on an as-needed basis, and/or may allow different types and/or amounts of bioactive agents to be provided to a patient from time to time.

Reservoirs may be preloaded with specific amounts of one or more bioactive agents, may be preloaded with a non-bioactive material (e.g., an inert gas or liquid), or may not be preloaded with anything at all. In some variations, a lead system including a reservoir that does not contain any bioactive agents may be at least partially implanted in a body of a subject. The reservoir may thereafter be partially or completely filled with one or more bioactive agents. In certain variations, a lead system including a reservoir that is preloaded with one or more bioactive agents may be at least partially implanted in a body of a subject, and the reservoir may thereafter be provided with one or more bioactive agents that are different from the bioactive agents with which the reservoir originally was preloaded.

Figure 5:
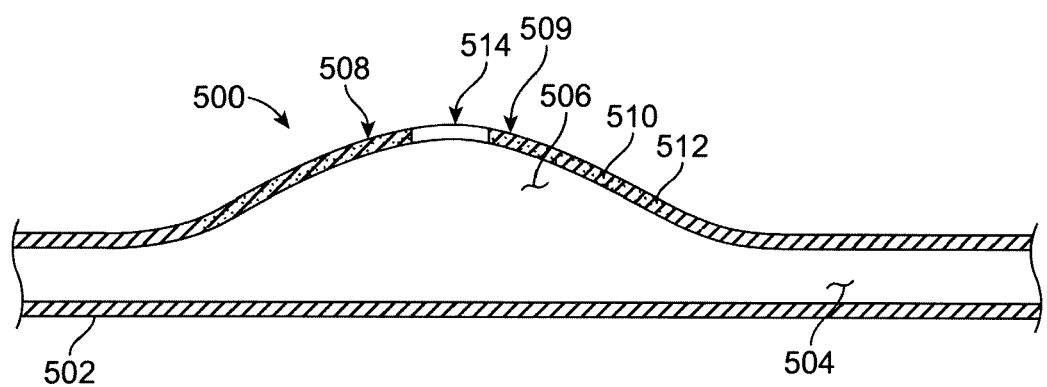

In certain variations, one or more portions of the sidewall of a reservoir may be reinforced or formed of a material that is different from the material used for one or more other portions of the sidewall of the reservoir. As an example, FIG. 5 shows a portion of a lead system (500) including a lead body (502) having a lumen (504), and a reservoir (506) that is integral with the lead body and in fluid communication with the lumen. Two portions (508) and (509) of the sidewall (510) of reservoir (506) are reinforced with a material (512). Material (512) enhances the strength and/or hardness of portions (508) and (509) relative to the injectable portion (514) of the sidewall, and may comprise, for example, a polyurethane or silicone material, or stainless steel or titanium. In some variations, portions (508) and (509) of sidewall (510) may be strengthened and/or hardened by embedding one or more biocompatible materials into the material or materials used for the rest of lead body (502) or sidewall (510). Similarly, a mesh material (e.g., formed of polyester or nylon) may be molded into sidewall (510), and may provide sidewall (510) with the advantage of an increased resistance to tearing. The presence of material (512) in portions (508) and (509) may limit the likelihood of a syringe being injected into a non-targeted portion of the reservoir, and/or may cause the reservoir to be relatively durable. This may be particularly useful, for example, if the reservoir is located outside of the subject's body, as described in further detail below.

While a reservoir having a portion that is configured for passage of a syringe needle therethrough has been described, in some variations, an entire reservoir may be formed of one or more materials that cause the reservoir to be configured for passage of a syringe needle therethrough. The reservoir may, for example, be formed of a material that allows a physician or patient to locate the reservoir by touch, while also allowing a syringe needle to be passed into the reservoir. While the syringe needle may form a puncture hole in the reservoir, the puncture hole may be relatively small, such that little or no bioactive agent can escape through it. Furthermore, the reservoir may include a material, such as silicone, that is capable of deforming to close a puncture hole (e.g., if a low-gauge needle is used). In some variations, a reservoir may include a rigid backing plate that serves as a needle stop, such that the rigid backing plate can prevent a syringe needle from over-penetrating the reservoir.

Figure 26A:
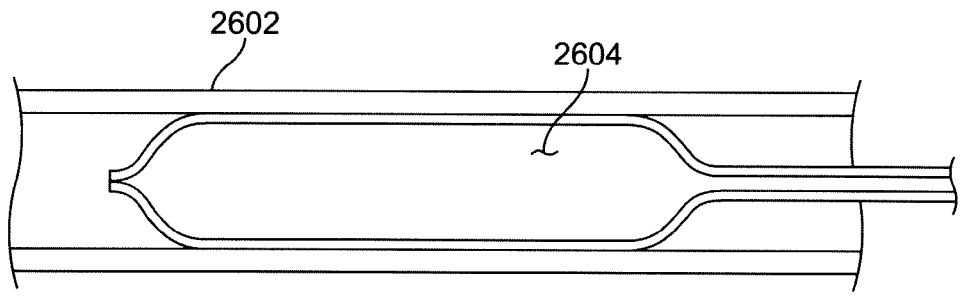
FIGS. 26A and 26B are cross-sectional views of a portion of a medical electrical lead system.
Figure 26B:
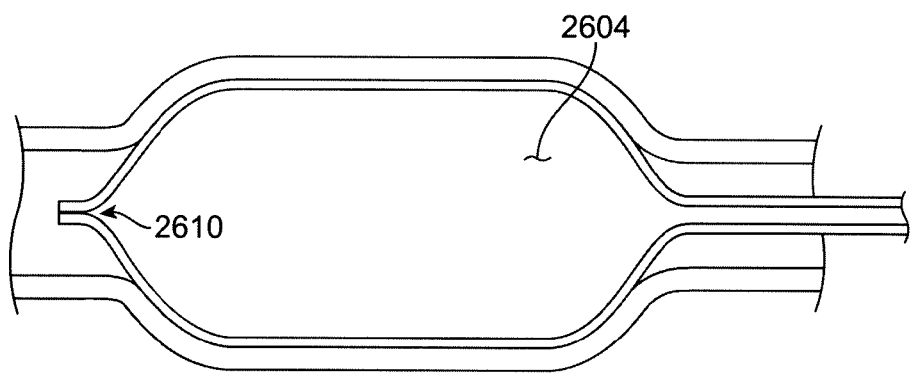

In certain variations, a reservoir of a lead system may be a plastic reservoir in the form of a bladder. A lead system including a bladder-type reservoir is shown in FIGS. 26A and 26B. A septum mechanism can be lacerated within the bladder to create a path for controlled liquid flow or dispersion. The lead body itself may be configured to comprise the plastic reservoir, for example, a section of the lead body may be formed with thinned walls in the portion that is to act as the bladder. Alternatively, the plastic reservoir can be provided so that it is disposed within the lead body. Referring to FIGS. 26A and 26B, a portion of lead body (2602) is shown having a plastic reservoir (2604) disposed therein. The plastic reservoir in FIGS. 26A and 26B is an inflatable bladder (2604), and is shown as deflated (e.g., substantially empty) in FIG. 26A, and inflated in FIG. 26B. The plastic reservoir is in fluid communication with one or more fill ports (not shown).

Figure 27A:
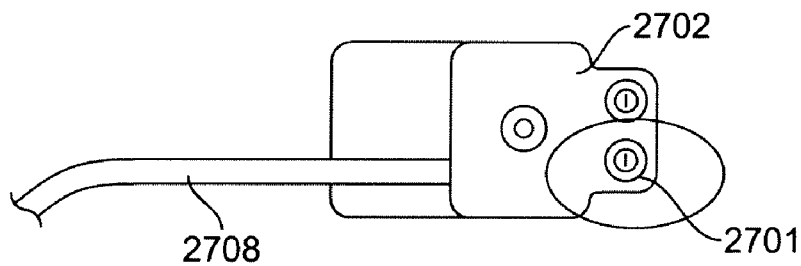
FIGS. 27A to 27C shows a fill port that may be used with a lead body.
Figure 27B:
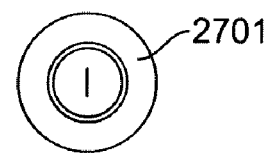
Figure 27C:
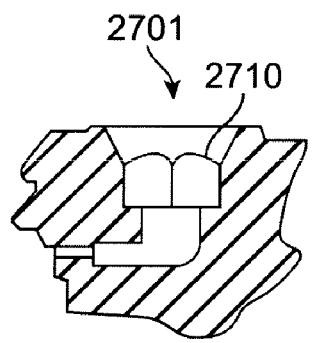
Figure 30A:
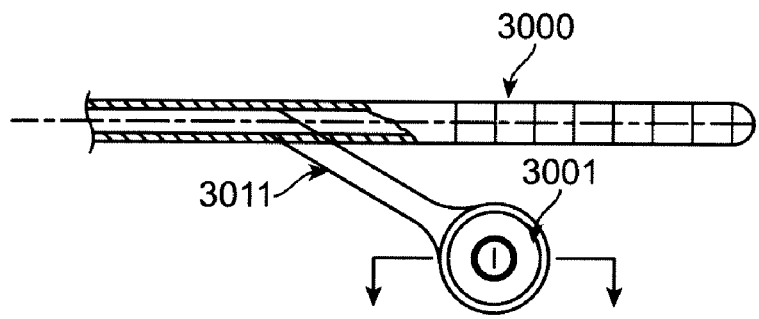
FIGS. 30A and 30B show portions of a medical electrical lead system as described herein.
Figure 30B:
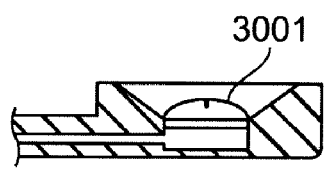

One variation of a fill port is shown in FIGS. 27A-27C. The fill port(s) can be provided at various locations as will be apparent to one skilled in the art, such as in a connector or cover (2702) in communication with the lead body (2708). FIG. 27B is a magnified view of the fill port (2701) indicated by the circled region in FIG. 27A, and FIG. 27C is a cross-sectional view through this fill port (2701). A septum or membrane (2710) can be provided between fill port and the interior of the reservoir. In another variation, a valve (2610) is provided to control the flow of fluid into and/or out of the reservoir, as shown in FIG. 26B. FIG. 30A shows another variation of a lead system (3000) having a fill port (3001). The fill port (3001) may act as a needle guide, providing a large injection surface into which the needle can be inserted. The fill port may include a needle stop at the bottom surface (opposite the injection side), to prevent the needle from penetrating beyond the septum of the port. In FIG. 30A and 30B, the needle port does not include a substantial reservoir itself, although is in fluid communication with the reservoir. In some variations, the needle port may include a reservoir. In FIG. 30A, the fill port is connected to the lead system by an enclosed passageway or tubing 3011, which may be of any appropriate length, allowing it to be positioned distally from the lead. FIG. 30B shows a cross-section through the fill port (3001).

Figure 6:
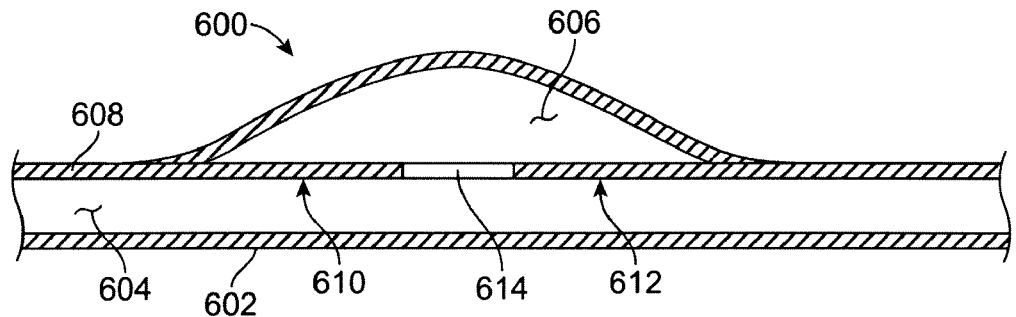

The above-described lead systems have been shown as including reservoirs that are in full fluid communication with the lumens of the lead bodies. However, in some variations, the fluid communication between a reservoir and a lumen of a lead body may be somewhat restricted. This may, for example, allow the reservoir to provide a bioactive agent to the lumen of the lead body over a prolonged period of time, rather than immediately. For example, FIG. 6 shows a portion of a lead system (600) including a lead body (602) having a lumen (604), and a reservoir (606) that is in fluid communication with the lumen. Lead body (602) includes a sidewall (608) having portions (610) and (612) that extend partially into reservoir (606), thereby limiting the fluid communication between reservoir (606) and lumen (604). However, there is an aperture (614) in sidewall (608) that allows the contents of reservoir (606) to flow into lumen (604). The size of aperture (614) may be selected, for example, based on the desired flow rate of bioactive agent into lumen (604). Typically, as the size of aperture (614) decreases, the flow rate of bioactive agent through aperture (614) will also decrease, depending on the characteristics of the bioactive agent. Similarly, as the size of aperture (614) increases, the flow rate of bioactive agent through aperture (614) generally will also increase. In some variations, aperture (614) can have a maximum dimension (e.g., a diameter) of from about one micron to about one centimeter. Aperture (614) may be circular in shape, but need not be. For example, aperture (614) may have an oval or square shape, or any other appropriate shape.

In certain variations, a membrane may be situated in aperture (614), and the permeability of the membrane may be selected to provide a desired bioactive agent flow rate through the aperture. The membrane may be constructed, for example, of permeable silicone or a similar material, and the diffusion or flow rate of bioactive agent through the membrane may be calculated using standard differential equation techniques. In another variation, the bioactive agent and the dimensions of aperture (614) may be specified so that the bioactive agent would remain in the reservoir unless and until pressure is applied internally to the reservoir to force the bioactive agent to move out of the reservoir. For example, an inorganic salt may be added to water-based bioactive agent to increase surface energy, or to an alcohol-based bioactive agent to decrease surface energy. Certain surfactants may also decrease the surface energy of water-based bioactive agents. In some variations, a syringe may be inserted into a syringe-injectable portion or septum of reservoir (606) (not shown), and may be used to fill reservoir (606) with a sufficient amount of bioactive agent so as to cause reservoir (606) to expand. The resulting internal fluid pressure and stretched reservoir wall may drive the bioactive agent through the membrane, thereby causing the bioactive agent to flow from the reservoir into the lead body. The result can be that a desired bioactive agent dosage may be provided to a target site over a desired duration of time.

Figure 7:
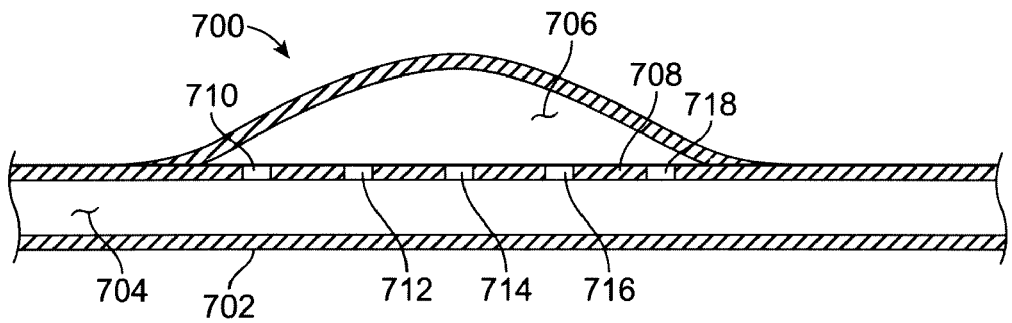

While the lead body of FIG. 6 includes only one aperture, lead bodies may include more than one aperture, such as two, three, four, five, or ten apertures. The apertures may be of the same size, or may have different sizes. For example, FIG. 7 shows a portion of a lead system (700) including a lead body (702) having a lumen (704), and a reservoir (706) that is in fluid communication with the lumen. The lead body has a sidewall (708) including five apertures (710), (712), (714), (716), and (718) that provide fluid communication between reservoir (706) and lumen (704).

Figure 8:
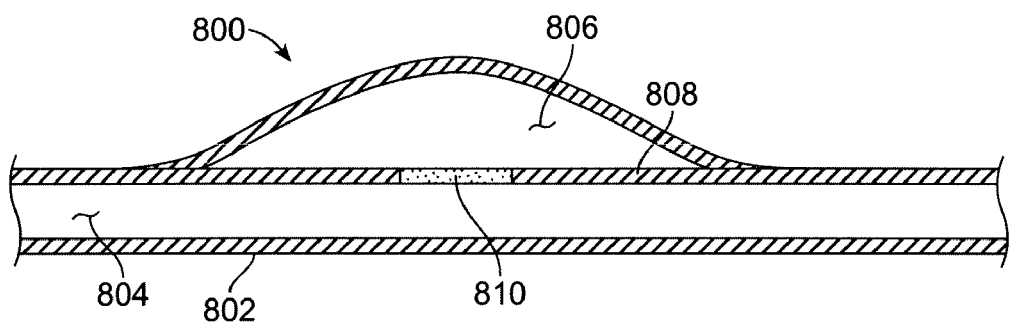

In certain variations, a lead body may include a permeable section that provides limited fluid communication between a reservoir and a lumen of the lead body. For example, FIG. 8 shows a lead system (800) including a lead body (802) having a lumen (804), and a reservoir (806). Lead body (802) has a sidewall (808) including a portion (810) that is formed of a permeable material, such as permeable silicone. The permeable material may be selected, for example, based on the bioactive agent or agents that are to be delivered through the lead system to a target site. In some variations, the permeable material may be selected based on its level of permeability. For example, if a relatively slow rate of bioactive agent release is desired, then a material having relatively low permeability for that bioactive agent may be selected for portion (810). By contrast, if a relatively high rate of bioactive agent release is desired, then a material having relatively high permeability for that bioactive agent may be selected for portion (810). In some variations in which lead body (802) (including portion (810)) is formed of polymers, lead body (802) may be formed using an extrusion process, such as an intermittent extrusion process.

Figure 9A:
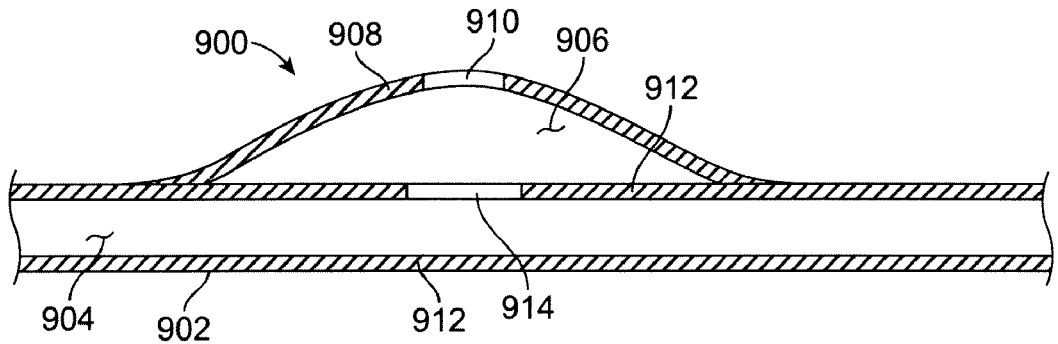
FIG. 9A is a cross-sectional view of a portion of a medical electrical lead system.
Figure 9B:
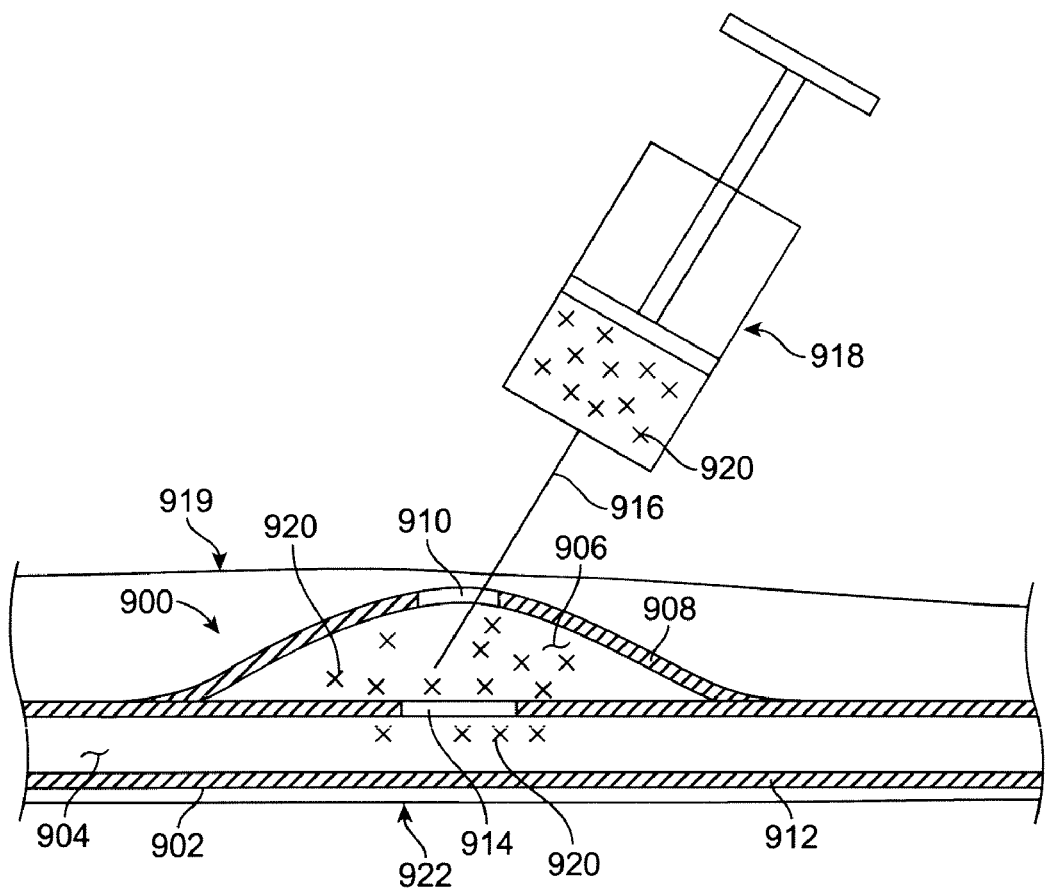
FIG. 9B illustrates the injection of a bioactive agent into a reservoir of the portion of the lead system of FIG. 9A.

As described above, some variations of methods may include injecting one or more bioactive agents into a reservoir of a lead system. FIGS. 9A and 9B demonstrate an example of such a method. As shown in FIG. 9A, a lead system (900) includes a lead body (902) having a lumen (904), and a reservoir (906) that is in fluid communication with the lumen. Reservoir (906) includes a sidewall (908) having a portion (910) that is configured for passage of a syringe needle therethrough. Lead body (902) has a sidewall (912) including an aperture (914), which provides for fluid communication between reservoir (906) and lumen (904). As shown in FIG. 9B, a needle (916) of a syringe (918) is inserted through a scalp (919) of a subject, and into reservoir (906) via portion (910). Syringe (918) is then used to inject a bioactive agent (920) into the reservoir. Because the reservoir is in fluid communication with the lumen, the bioactive agent passively advances from the reservoir into the lumen, through aperture (914).

As shown in FIG. 9B, lead system (900) is implanted between a cranium (922) of a subject and the scalp (919) of the subject. This may allow for relatively easy injection of the bioactive agent into the reservoir. For example, a physician may simply feel the subject's scalp to determine the exact location of the reservoir, and then inject bioactive agent into the reservoir directly through the scalp. Furthermore, some variations of lead systems may include reservoirs having identifying markers (e.g., formed of MRI-visible and/or radiopaque materials) that may allow the reservoirs (and their syringe-injectable portions, if applicable) to be relatively easily located. The syringe-injectable portion of a reservoir may have a sufficiently large area to allow syringe needles to be inserted into different regions of the syringe-injectable portion. This may, for example, limit the likelihood of syringe needles being inserted into the same location of the syringe-injectable portion so many times that the needle tears up the syringe-injectable portion.

In certain variations, the dimensions of a lead system, such as lead system (900), may be selected to provide the lead system with a relatively low profile, so that the lead system is not easily visible from the outside when the lead system is implanted within a subject's head (e.g., so that the lead system does not form a protrusion on the subject's head). Moreover, some variations of lead systems may include a reservoir that is configured to be implanted in a skull of a subject. This may, for example, prevent the reservoir from forming a visible protrusion on a subject's head when it is implanted in the subject's skull.

In some variations, a lead system may include one or more features that allow for controlled, regulated release of bioactive agent from a reservoir of the lead system. Certain variations of lead systems may be configured to deliver bioactive agents to a target site intermittently, over selected periods of time, such as every ten minutes, every hour, or every day. In some variations, and as described briefly above, a lead system may include one or more valves that control release of bioactive agent. The valves may be, for example, one-way valves that prevent the bioactive agent from re-entering the reservoir after the bioactive agent has exited the reservoir and entered the lumen. The valves may allow the bioactive agent to passively advance through the lead system, or may be used in conjunction with one or more other components, such as a pump, that actively advance the bioactive agent through the lead system.

Figure 10A:
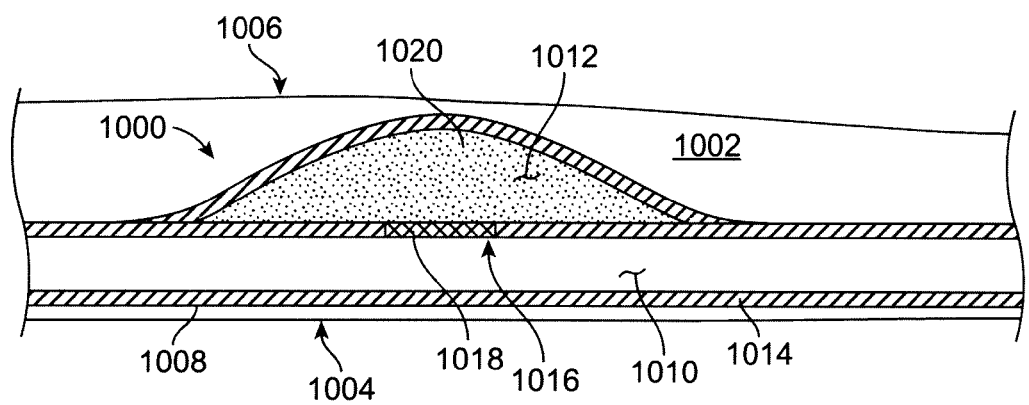
FIG. 10A is a cross-sectional view of a portion of a medical electrical lead system.
Figure 10B:
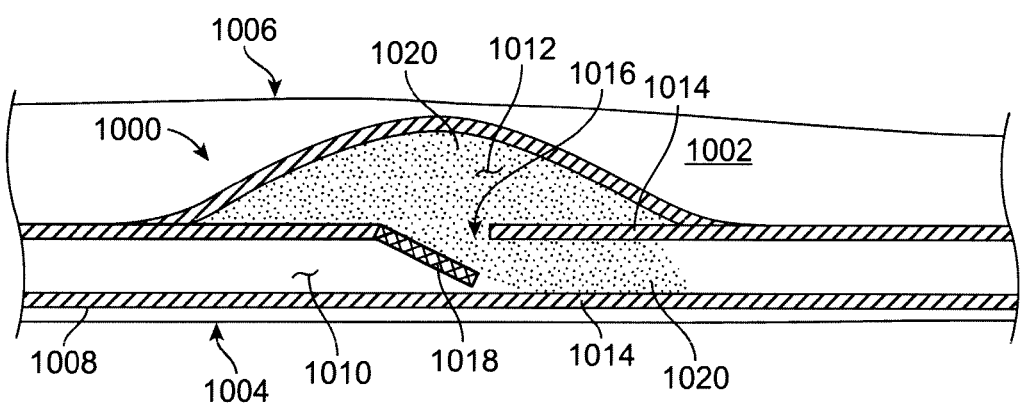
FIG. 10B illustrates the activation of a valve in the portion of the lead system of FIG. 10A.

An example of a lead system including a valve in shown in FIGS. 10A and 10B. As shown in FIG. 10A, a lead system (1000), which is implanted into a space (1002) between a cranium (1004) and a scalp (1006) of a subject, includes a lead body (1008) having a lumen (1010), and a reservoir (1012). Lead body (1008) has a sidewall (1014) with an aperture (1016) that is sealed by a valve (1018). When the valve is sealed, it prevents bioactive agent (1020) from advancing from reservoir (1012) into lumen (1010). However, and as shown in FIG. 10B, when valve (1018) is opened, bioactive agent (1020) flows from reservoir (1012) into lumen (1010). In some variations, a valve such as valve (1018) may be magnetically activated, such that the valve can be opened by a magnet that is placed in the vicinity of the valve. For example, a magnet may be swiped by scalp (1006), in the vicinity of the position of lead system (1000), to open valve (1018). In this way, the release of bioactive agent from the reservoir may be controlled as desired. In some variations, the valve itself may include one or more magnets. Furthermore, while certain valve mechanisms have been described, other methods and mechanisms for activating a valve are contemplated, as would be apparent to those skilled in the art. Moreover, it should be understood that while a lead system with one valve is shown, lead systems may include more than one valve, such as two, three, four, or five valves.

While lead systems with valves for regulation of bioactive agent delivery have been described, in some variations, regulation of bioactive agent delivery may be achieved using one or more other methods. As an example, in certain variations, bioactive agents may be delivered from a reservoir of a lead system and into a lead body of the lead system by electrostatically drawing the bioactive agents out of the reservoir at a predictable rate, as described previously herein. As another example, in some variations, ultrasound may be used to cause bioactive agent to move through a lead system (e.g., from a reservoir into a lead body) and/or from a lead system into a target site. For example, a lead system may include a reservoir containing a bioactive agent, a lead body, and a membrane separating the reservoir from the lead body. Cavitating gas bodies, such as microbubbles, that may be produced by ultrasound, may disrupt the structure of the membrane and increase its permeability, thereby allowing bioactive agent to flow out of the reservoir and into the lead body.

Figure 11:
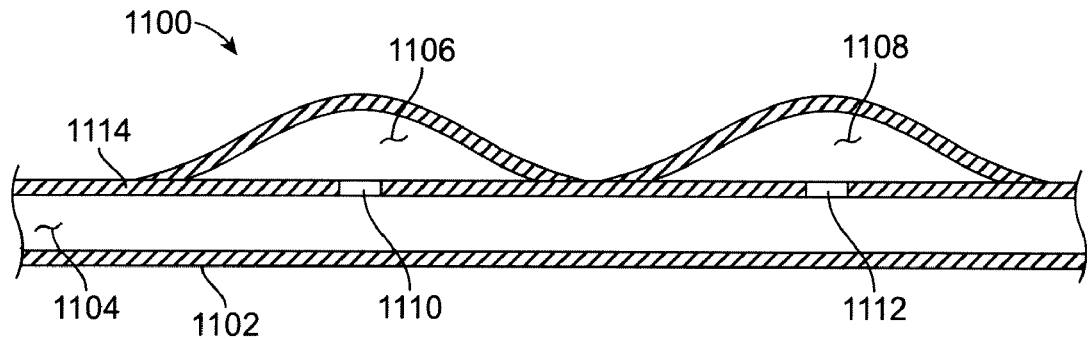
FIGS. 11-19 are cross-sectional views of portions of medical electrical lead systems.
Figure 12:
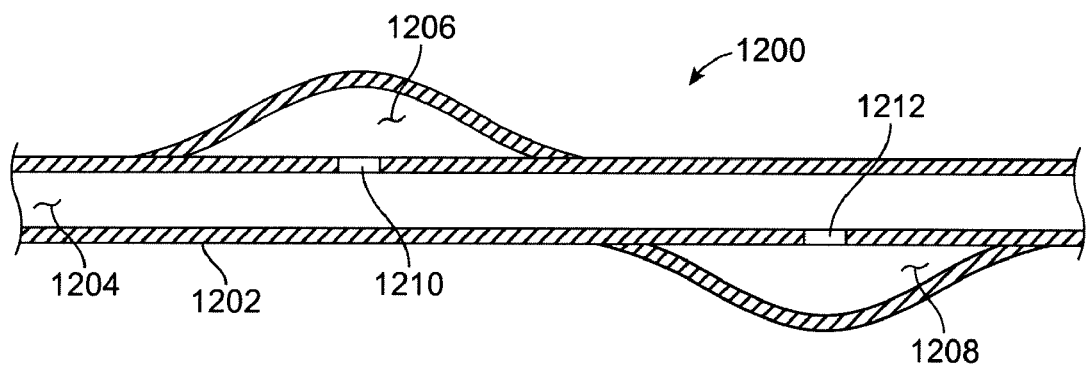
Figure 13:
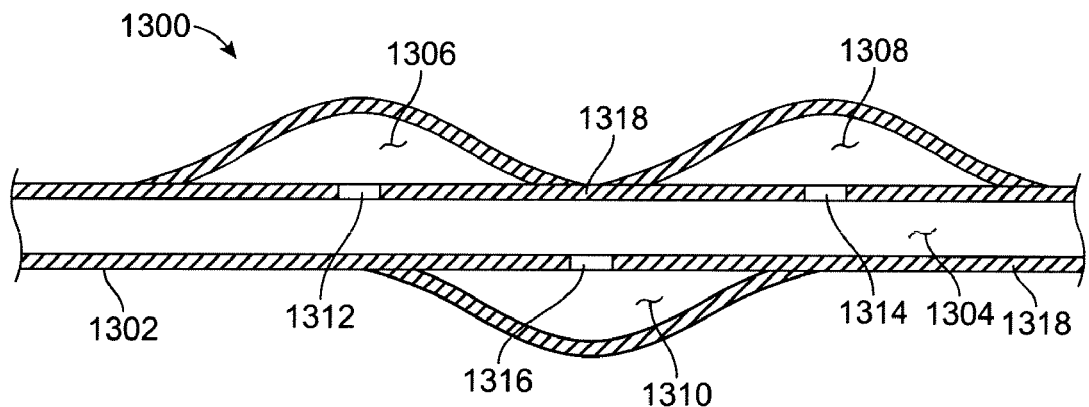

Furthermore, while lead systems with one reservoir have been shown, some variations of lead systems may include more than one reservoir, such as two, three, four, or five reservoirs. For example, FIG. 11 shows a lead system (1100) including a lead body (1102) with a lumen (1104), and two reservoirs (1106) and (1108) that each are in fluid communication with lumen (1104). The reservoirs are in fluid communication with the lumen because of two apertures (1110) and (1112) in the sidewall (1114) of the lead body. As shown in FIG. 11, reservoirs (1106) and (1108) are both located in the same region of lead body (1102), and are next to each other. However, reservoirs may be located in different regions of a lead body, and/or may not be next to each other. As an example, FIG. 12 shows a lead system (1200) including a lead body (1202) having a lumen (1204), and two reservoirs (1206) and (1208) that are in fluid communication with lumen (1204). Reservoirs (1206) and (1208) are located in regions of lead body (1202) that are opposite each other. Apertures (1210) and (1212) allow the reservoirs to be in fluid communication with the lumen of the lead body. As another example, FIG. 13 shows a lead system (1300) including a lead body (1302) having a lumen (1304), and three reservoirs (1306), (1308), and (1310) that are in fluid communication with the lumen via apertures (1312), (1314), and (1316), respectively, in a sidewall (1318) of the lead body. Reservoirs (1306) and (1308) are located on one side of the lead body, while reservoir (1310) is located on an opposite side of the lead body.

Figure 14:
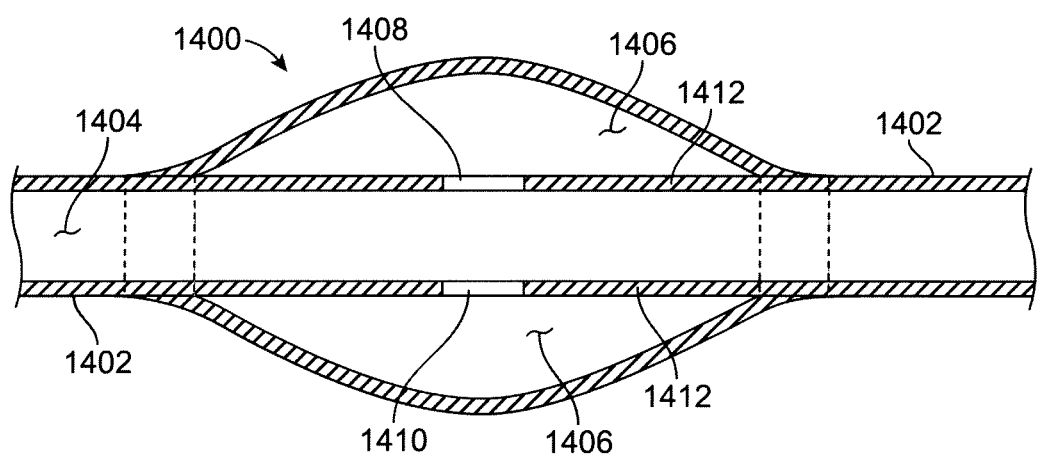

In certain variations, a reservoir may surround a portion of a lead body. For example, FIG. 14 shows a lead system (1400) including a lead body (1402) having a lumen (1404), and a reservoir (1406). Reservoir (1406) surrounds a portion of lead body (1402), and is in fluid communication with lumen (1404) via apertures (1408) and (1410) in a sidewall (1412) of lead body (1402). One advantage to lead system (1400) may be that reservoir (1406) is relatively easily located for filling or refilling of a bioactive agent. More specifically, if the location of reservoir (1406) along the lead body is known, then reservoir (1406) may be relatively easily injected with a bioactive agent, regardless of the orientation of lead system (1400).

Figure 15:
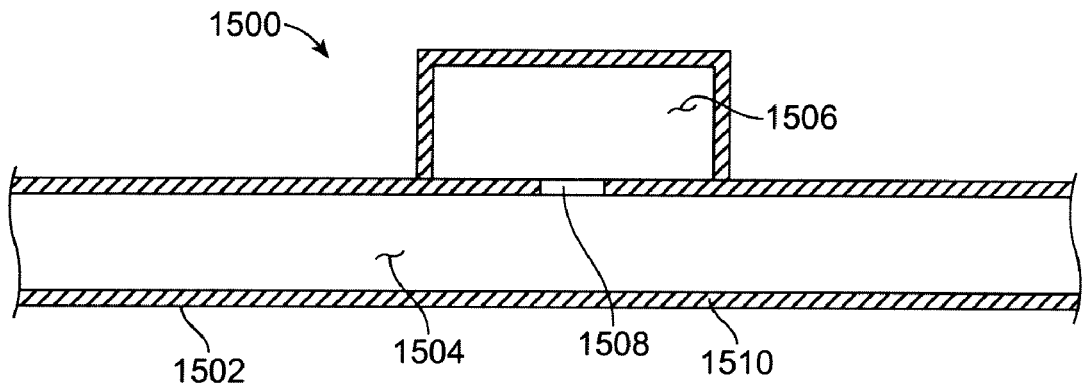

While reservoirs in the form of generally rounded protrusions have been shown, any suitable configuration, size, and shape of reservoir may be employed in a lead system. As an example, FIG. 15 shows a lead system (1500) including a lead body (1502) having a lumen (1504), and a reservoir (1506) that is in fluid communication with lumen (1504) via an aperture (1508) in a sidewall (1510) of lead body (1502). As shown in FIG. 15, reservoir (1506) has a rectangular cross-section. However, reservoirs may have other cross-sectional shapes, such as triangular, trapezoidal, irregular, etc. Similarly, a lead body may have any of a number of different cross-sectional shapes, such as a generally circular cross-sectional shape, a triangular cross-sectional shape, etc. In some variations, a lead body may have one cross-sectional shape (e.g., generally circular) in the area of a reservoir, but may have another cross-sectional shape (e.g., square) in a different area.

Figure 16:
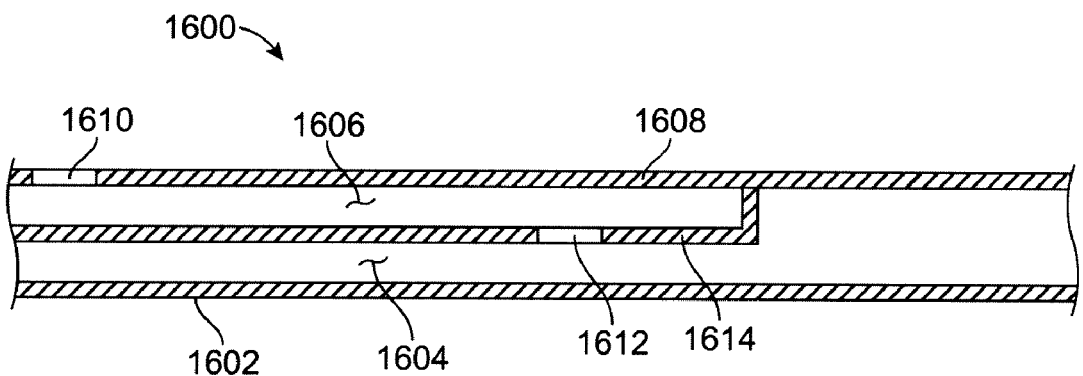
Figure 17:
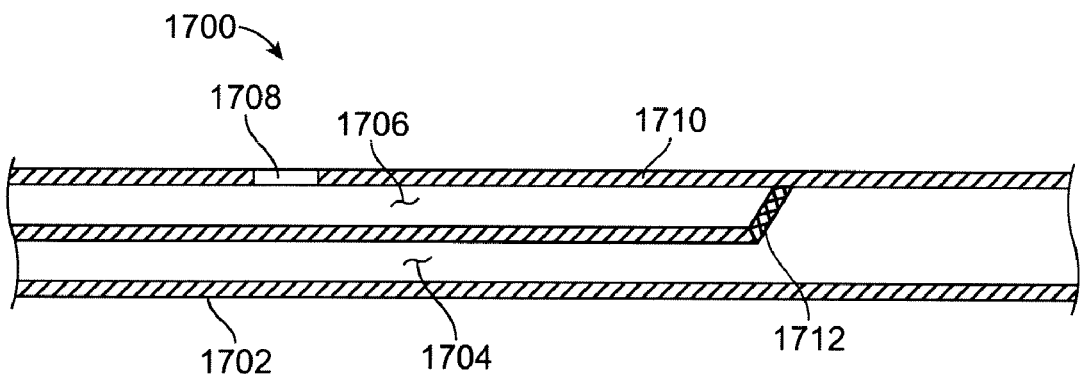

Furthermore, while reservoirs in the form of protrusions have been shown, reservoirs may have other forms. For example, FIG. 16 shows a lead system (1600) including a lead body (1602) having a first lumen (1604), and a reservoir in the form of a second lumen (1606) of lead body (1602). Lead body (1602) further includes a sidewall (1608) having a section (1610) that is configured for injection of a syringe needle. The syringe needle may be used to deliver one or more bioactive agents into second lumen (1606). These bioactive agents may, in turn, flow from second lumen (1606) into first lumen (1604) via an aperture (1612) in a sidewall (1614) of lead body (1602). Similarly, FIG. 17 shows a lead system (1700) including a lead body (1702) having a first lumen (1704), and a reservoir in the form of a second lumen (1706) of the lead body. A syringe needle may be used to deliver one or more bioactive agents into second lumen (1706) via a section (1708) of the sidewall (1710) of lead body (1702). Second lumen (1706) and first lumen (1704) are separated from each other by a valve (1712) that may be opened to release bioactive agent from the second lumen into the first lumen. Reservoirs that are in the form of lumens may allow a lead system to maintain a consistent profile, among other advantages.

Figure 18:
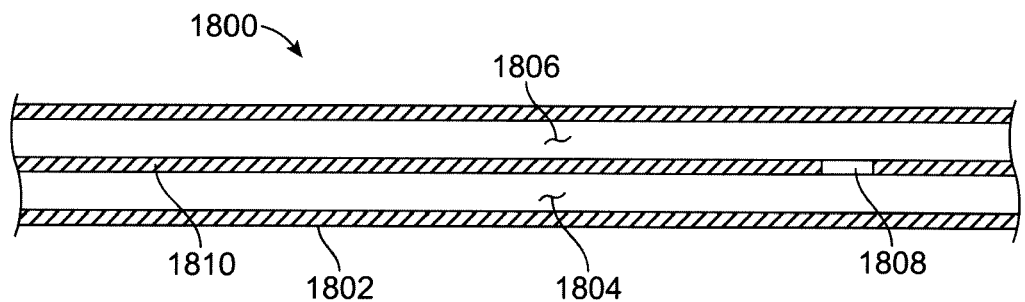

While reservoirs in the form of lumens extending only partially along the length of a lead body have been shown, some reservoirs may be in the form of a lumen that extends along the entire length of a lead body. For example, FIG. 18 shows a lead system (1800) including a lead body (1802) having a first lumen (1804), and a reservoir in the form of a second lumen (1806). Second lumen (1806) extends along the entire length of lead body (1802), and is in fluid communication with first lumen (1804) via an aperture (1808) in a sidewall (1810) between the first and second lumens. In some variations, a reservoir in the form of a lumen that extends along the entire length of a lead body may be used to store a relatively large amount of bioactive agent. Accordingly, the reservoir may not need to be refilled, or may only need to be refilled infrequently.

Figure 19:
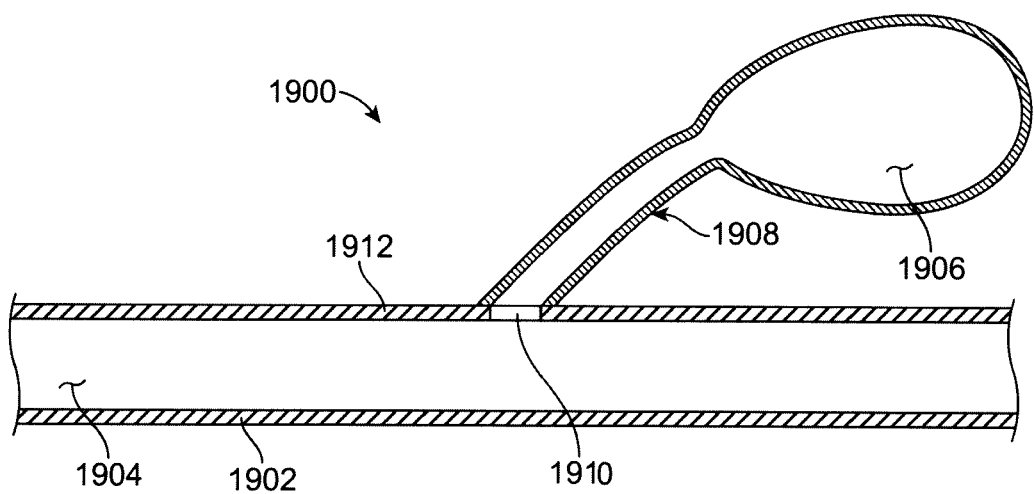

Certain variations of lead systems may include reservoirs that are removed from the lead body. For example, FIG. 19 shows a lead system (1900) including a lead body (1902) having a lumen (1904). Lead system (1900) further includes a reservoir (1906) that is in fluid communication with lumen (1904) via tubing (1908) and an aperture (1910) in a sidewall (1912) of lead body (1902). Lead system (1900) may be positioned, for example, such that reservoir (1906) is relatively easily accessed for refilling of bioactive agent.

Figure 20A:
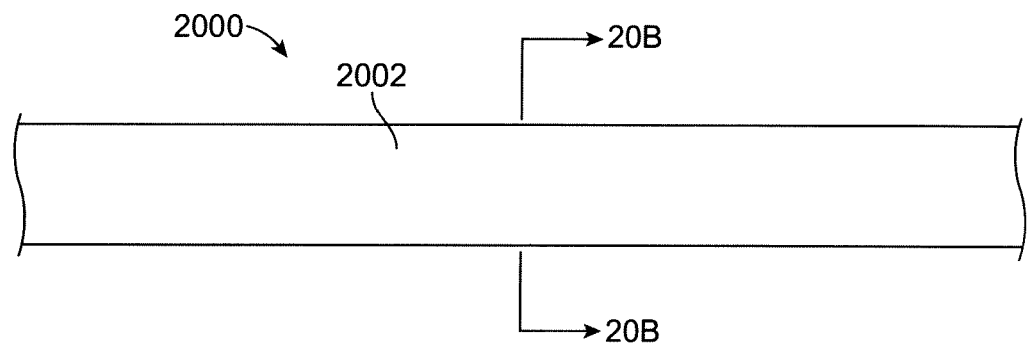
FIG. 20A is a side view of a portion of a medical electrical lead system.
Figure 20B:
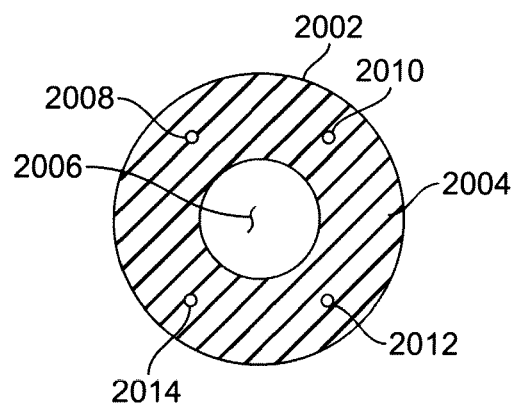
FIG. 20B is a cross-sectional view of the portion of the lead system of FIG. 20A, taken along line 20B-20B.
Figure 28:
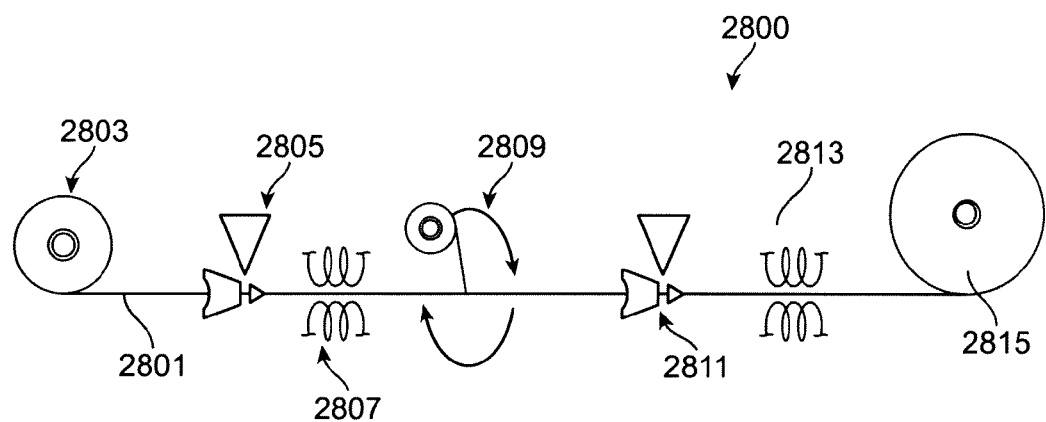
FIG. 28 illustrates a method of fabricating a medical lead system as described herein.
Figure 29:
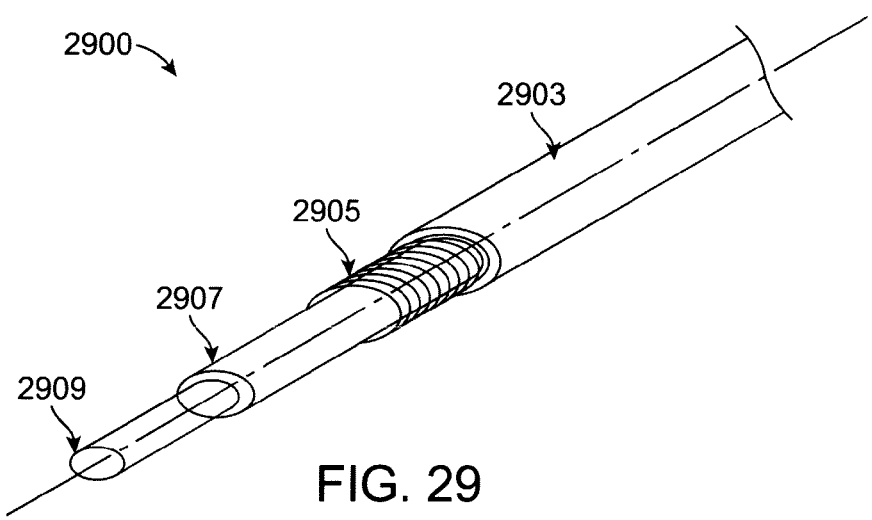
FIG. 29 is a cut-away projection of a portion of a medical electrical lead system.

As discussed above, lead systems include one or more conductors that may be used to provide an electrical connection between a medical device and the electrodes on the lead systems. FIGS. 20A and 20B show one variation of a lead system including conductors. As shown in FIG. 20A, a lead system (2000) includes a lead body (2002). Referring now to FIG. 20B, lead body (2002) includes a sidewall (2004) and a lumen (2006) defined by the sidewall. Conductive wires (2008), (2010), (2012), and (2014) are embedded in sidewall (2004). Methods of embedding conductors in the sidewall of lumens of implantable medical devices are well known. FIG. 28 is a schematic illustration of one method of forming a lead system (2800) having an embedded conductor and a lumen. FIG. 29 shows a cut-away perspective view of a portion of a lead system similar to a lead that may be formed by the method illustrated in FIG. 28. In FIG. 28, a coiled conductor is embedded, although straight conductors may also be used. The material used for the conductor can be wire or some other conductive material such as a conductive thread. With this manufacturing method a mandrel (2801) from a mandrel spool (2803) is drawn through a system (2800). As the mandrel is drawn through a first nozzle (2805), a base insulation layer is extruded onto the mandrel from the first nozzle. The material is cured in cure-oven (2807) when thermo-set is used. An orbital spooler (2809) winds a conductor (or reinforcement wire in some variations) around the coated mandrel. A second (or more) layer of insulation is then extruded on top of the conductor by cap layer extruder (2811), and the insulation is then cured by the second cure oven (2813). After curing, the formed material may be wound onto a spool (2815) for later use. For example, segments may then be cut to a desired length and the segments removed from the mandrel (e.g., by stretching the mandrel between arbors to reduce its diameter). The cutaway perspective view shown in FIG. 29 shows a lead system (2900) including an outer protective insulation layer (2903) covering a coiled conductor (2905) that wraps around the base insulation layer (2907), covering the mandrel (2909).

Figure 21A:
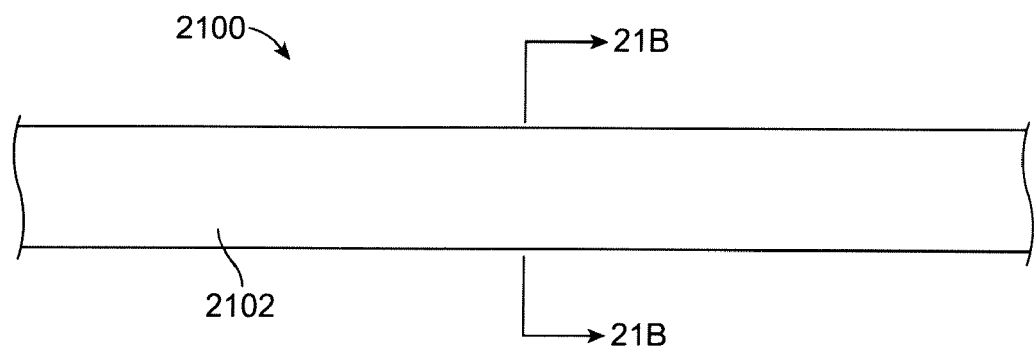
FIG. 21A is a side view of a portion of a medical electrical lead system.
Figure 21B:
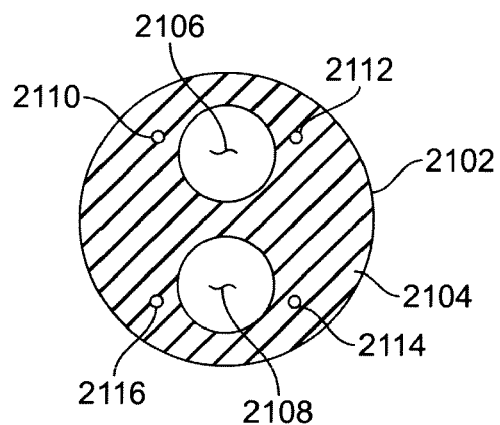
FIG. 21B is a cross-sectional view of the portion of the lead system of FIG. 21A, taken along line 21B-21B.

Similarly, FIG. 21A shows a lead system (2100) including a lead body (2102). As shown in FIG. 21B, lead body (2102) has a sidewall (2104) defining two lumens (2106) and (2108). Four conductive wires (2110), (2112), (2114), and (2116) are embedded in sidewall (2104).

While lead systems including four conductive wires have been shown, lead systems may include any number of conductive wires, such as one, two, three, four, five, or ten conductive wires. One or more of the wires may extend straight through the sidewall of a lead body, and/or may wind or coil around a lumen or lumens within the lead body. In some variations, one or more conductive wires may be situated within a lumen of a lead body. In such variations, the conductive wires may be coated or sheathed within a non-conductive and/or protective material, such as silicone, polyurethane, or polyethylene.

Figure 22A:
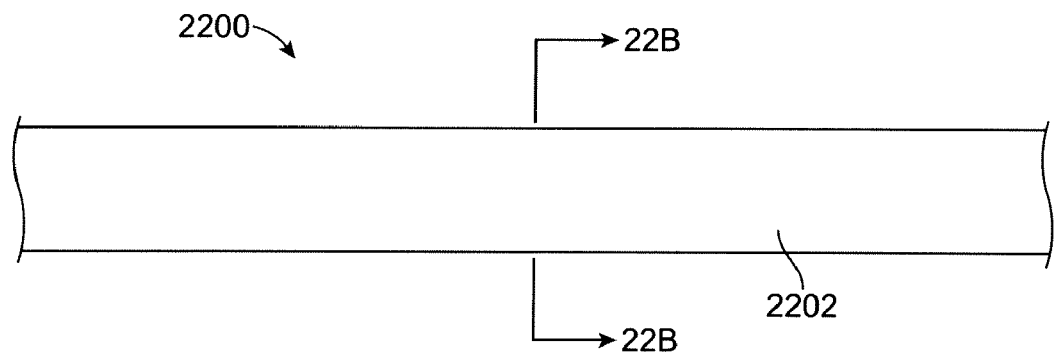
FIG. 22A is a side view of a portion of a medical electrical lead system.
Figure 22B:
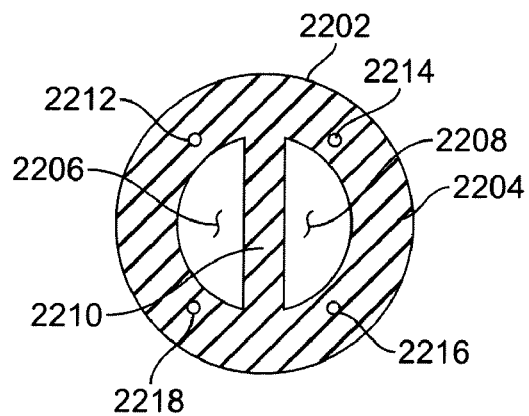
FIG. 22B is a cross-sectional view of the portion of the lead system of FIG. 22A, taken along line 22B-22B.

Moreover, while lumens having a circular cross-section have been shown, in some variations, a lead body can include one or more lumens having a non-circular cross-section. For example, FIG. 22A shows a lead system (2200) including a lead body (2202). As shown in FIG. 22B, lead body (2202) includes a sidewall (2204) and two lumens (2206) and (2208) having crescent-shaped cross sections and separated by a dividing wall (2210). Four conductive wires (2212), (2214), (2216), and (2218) are embedded in sidewall (2204). Other cross-sectional shapes may be used for lumens of lead bodies, including, for example, triangular, rectangular (e.g., square), irregular, etc.

Figure 23:
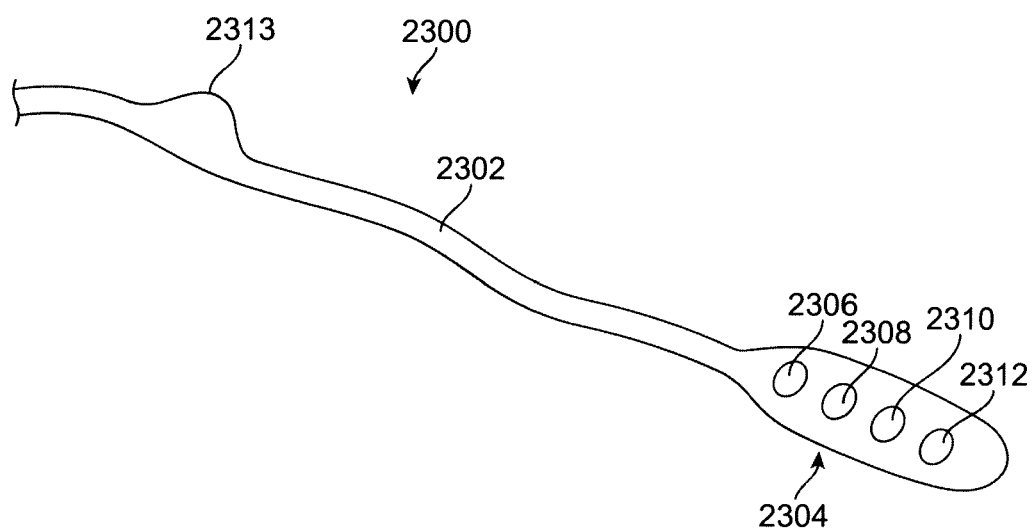
FIG. 23 is a top view of a portion of a medical electrical lead system.

While a lead system comprising a depth lead has been described with reference to FIG. 2 above, other types of lead systems, such as branched depth electrodes, and two-dimensional electrode arrays, may include reservoirs. For example, referring to FIG. 23, a lead system (2300) includes a lead body (2302) having an enlarged end portion (2304) enclosing four disc electrodes (2306), (2308), (2310), and (2312). Lead system (2300) further includes a reservoir (2313) that is integral with lead body (2302). Lead system (2300) is a cortical strip lead, and may, for example, be positioned on a surface of brain tissue during use.

Figure 24:
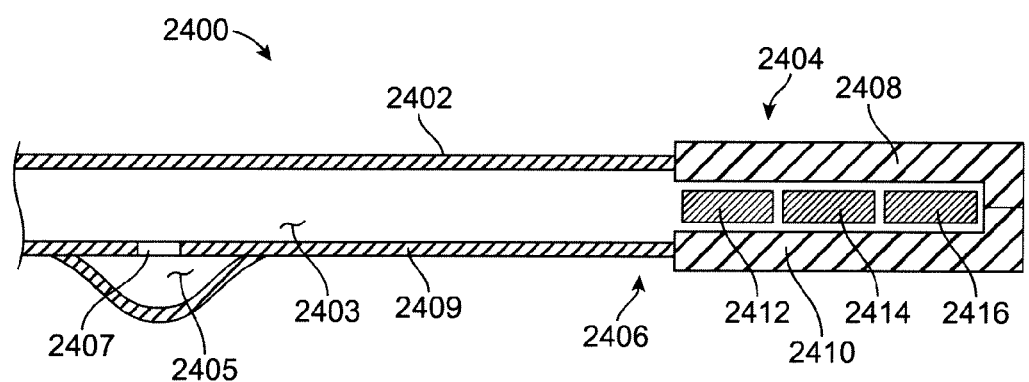
FIG. 24 is a cross-sectional view of a portion of a medical electrical lead system.

FIG. 24 shows a cross-sectional view of a lead system (2400) that is a cortical strip lead, as well. As shown in FIG. 24, lead system (2400) includes a lead body (2402) having a lumen (2403) and an electrode portion (2404) at its distal end (2406). Lead system (2400) further includes a reservoir (2405) that is in fluid communication with lumen (2403) via an aperture (2407) in a sidewall (2409) of lead body (2402). Electrode portion (2404) is formed of two portions (2408) and (2410) of material enclosing three electrodes (2412), (2414), and (2416). The electrodes are connected to conductors (not shown) that run through the length of the lead body. Portion (2408) and/or portion (2410) may be formed of one or more permeable materials, such as permeable silicone, or may be formed of one or more substantially impermeable materials, such as substantially impermeable silicone. For example, in some variations, portion (2408) may be formed of a permeable material, while portion (2410) may be formed of substantially impermeable material. In such variations, portion (2408) may be positioned such that it contacts brain tissue, while portion (2410) may be positioned such that it contacts the dura mater. The portions may be positioned this way, for example, to enhance the delivery of bioactive agents into the brain tissue.

The above-described lead systems may be positioned such that their reservoirs are located within a body of a subject (e.g., between the cranium and the scalp), or outside of a body of a subject (e.g., secured externally to the head of the subject), or such that some of the reservoirs are located within a body of a subject, while others are located outside of the body of the subject. Locating the reservoirs within the body of a subject may, for example, provide the reservoirs with enhanced protection, and/or may reduce the likelihood of the reservoirs being damaged from inadvertent contact. Locating the reservoirs outside of the body of a subject may enhance the accessibility of the reservoirs, making them relatively easy to fill or refill with bioactive agent as needed. In certain variations, a reservoir that is at least partially located outside of a body of a subject may be reinforced (e.g., as described with reference to FIG. 5 above). Alternatively or additionally, the reservoir may be of a different color from the lead body, so that the reservoir can be relatively easily located (e.g., for injection of a bioactive agent). For example, the reservoir may be red, while the lead body is clear. In some variations, the position of a reservoir may be selected to limit the likelihood of underlying tissue becoming damaged as a result of a scalp injection.

In certain variations, a lead system may include a reservoir that is in fluid communication with a bioactive agent delivery lumen or port. In such variations, the lumen or port may be positioned outside of the body of a subject, while the reservoir is positioned within the body of the subject. Bioactive agents may be delivered relatively easily into the lumen or port, which can then provide the reservoir with the bioactive agents. Lumens or ports may alternatively be located within a body of a subject.

In some variations of lead systems including a reservoir in the form of a protrusion, a subject or the subject's physician may be able to press down on the reservoir so that the reservoir temporarily releases more bioactive agent. This may be helpful, for example, if the subject begins to notice early warning signs that a seizure is impending, and wants to provide immediate treatment to prevent the seizure or to limit its severity.

While reservoirs that are integral with lead bodies have been described above, some variations of lead systems may include one or more reservoirs and lead bodies that are not integral with each other. As an example, a lead system may include a reservoir that is formed separately from its lead body and then attached to its lead body. Such a lead system may be formed, for example, by molding a biocompatible plastic coupling into either the reservoir or the lead body, and then force-fitting the reservoir onto the lead body. Transfer molding involves a hydraulic or pneumatic press having lower platen and upper platen. Uncured silicone rubber is placed into a reservoir within the lower platen. A mold, a book-mold in our case, is placed on top of the lower platen. The mold has an opening in its underside, matching the opening location in the reservoir, to receive the material. When the press is actuated the upper platen engages the topside of the mold and applies pressure. A piston contained within the reservoir is actuated and transfers the material from the reservoir into a cavity within the mold. The upper and lower platens are heated and the rubber cures. When the cure process is complete the press disengages and the mold is removed from the press to recover the finished component. In some variations, a silicone lead body and reservoir may be formed separately, and then a silicone adhesive may be used to couple the reservoir to the lead body. In certain variations, a polyurethane lead body and reservoir may be formed separately, and then may be coupled to each other by adhesive-bonding and/or thermal-bonding methods.

Moreover, while lead systems that are directly connected to neurostimulation devices have been described, in certain variations, a lead system may be indirectly connected to an implantable medical device. For example, a lead system may be wirelessly connected to an implantable medical device.

While the methods and devices have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the appended claims.

What is claimed is:

1. A medical electrical lead system configured to be at least partially implanted in a body of a subject, comprising:
    a lead body comprising a proximal end and a distal end and a first lumen extending at least partially therebetween;
    at least one electrode in the proximity of the distal end of the lead body; and
    a reservoir in fluid communication with the first lumen and in the form of a second lumen of the lead body or a protrusion extending from the first lumen of the lead body, wherein the protrusion is configured to be refilled whether the protrusion is implanted in the body of the subject or external to the body of the subject during use,
    wherein the reservoir is located at a position removed from the distal end of the lead body.

2. The lead system of claim 1, wherein the lead system is configured to be at least partially implanted in neural tissue of a subject.

3. The lead system of claim 2, wherein the lead system is configured to be at least partially implanted in a brain of a subject.

4. The lead system of claim 1, wherein the reservoir is located in the proximity of the proximal end of the lead body.

5. The lead system of claim 1, wherein the reservoir is configured to be activated by a pump.

6. The lead system of claim 1, wherein the reservoir is in the form of a protrusion extending from the first lumen of the lead body, wherein the protrusion is configured to be refilled whether the protrusion is implanted in the body of the subject or external to the body of the subject during use.

7. The lead system of claim 6, wherein the protrusion extends from the first lumen of the lead body and surrounds a portion of the lead body.

8. The lead system of claim 1, wherein the lead system is configured to allow at least one bioactive agent to passively advance from the reservoir through the first lumen of the lead body.

9. The lead system of claim 1, wherein the lead system is configured for release of at least one bioactive agent therefrom by at least one of diffusion, elution, or effusion.

10. The lead system of claim 1, wherein the reservoir is configured to be secured to a skull of a subject.

11. The lead system of claim 1, further comprising at least one conductor disposed within the lead body.

12. The lead system of claim 11, wherein the at least one conductor is wound around the first lumen.

13. The lead system of claim 12, wherein the at least one conductor is coiled around the first lumen.

14. The lead system of claim 1, wherein the distal end of the lead body is formed of at least one permeable material.

15. The lead system of claim 14, wherein the proximal end of the lead body is formed of at least one substantially impermeable material.

16. The lead system of claim 1, wherein the proximal end of the lead body is formed of at least one substantially impermeable material.

17. The lead system of claim 1, wherein the lead system is configured to be connected to an implantable medical device.

18. The lead system of claim 1, wherein the lead body is integral with the reservoir.

19. The lead system of claim 1, wherein the reservoir is in the form of a second lumen of the lead body.

20. The lead system of claim 19, wherein the reservoir is refillable.

21. The lead system of claim 1, further comprising a valve located between the reservoir and the first lumen.

22. The lead system of claim 21, wherein the valve comprises a check valve.

23. The lead system of claim 1, wherein the reservoir comprises MRI-visible markers.

24. The lead system of claim 1, wherein the reservoir comprises radiopaque markers.

* * * * *